US012694975B2

(12) United States Patent
Vera-Ciro et al.

(10) Patent No.: US 12,694,975 B2
(45) Date of Patent: ***Jul. 28, 2026

(54) CONVERTING TABULAR DEMOGRAPHIC INFORMATION INTO AN EXPORT ENTITY FILE

(71) Applicant: H1 Insights, Inc., New York, NY (US)

(72) Inventors: Carlos Vera-Ciro, Madison, WI (US); Robert Lindner, Fitchburg, WI (US)

(73) Assignee: H1 Insights, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/891,329

(22) Filed: Sep. 20, 2024

(65) Prior Publication Data

US 2025/0232868 A1     Jul. 17, 2025

Related U.S. Application Data

(63) Continuation of application No. 18/114,026, filed on Feb. 24, 2023, now Pat. No. 12,142,368.

(60) Provisional application No. 63/268,537, filed on Feb. 25, 2022.

(51) Int. Cl.
| | |
|---|---|
| *G06F 16/25* | (2019.01) |
| *G06F 11/07* | (2006.01) |
| *G06F 40/194* | (2020.01) |
| *G16H 40/20* | (2018.01) |

(52) U.S. Cl.
CPC ......... *G16H 40/20* (2018.01); *G06F 11/0766* (2013.01); *G06F 16/258* (2019.01); *G06F 40/194* (2020.01)

(58) Field of Classification Search
CPC ..... G16H 40/20; G06F 16/258; G06F 40/194; G06F 11/0766
See application file for complete search history.

(56) References Cited

U.S. PATENT DOCUMENTS

| | | | | |
|---|---|---|---|---|
| 10,521,456 | B2 | 12/2019 | Lindner | |
| 2013/0151280 | A1* | 6/2013 | Thiers ................... | G16H 10/20 |
| | | | | 705/2 |
| 2013/0304510 | A1 | 11/2013 | Chen et al. | |
| 2018/0039735 | A1 | 2/2018 | Zhen et al. | |
| 2018/0060418 | A1 | 3/2018 | Robichaud | |
| 2019/0311299 | A1 | 10/2019 | Lindner | |

(Continued)

OTHER PUBLICATIONS

International Search Report and Written Opinion of the International Searching Authority for International Application No. PCT/US2023/063199, mailed Jun. 7, 2023; 9 pages.

*Primary Examiner* — Ajay M Bhatia
*Assistant Examiner* — Cindy Nguyen
(74) *Attorney, Agent, or Firm* — Sterne, Kessler, Goldstein & Fox P.L.L.C.

(57) ABSTRACT

The present disclosure is directed to methods and non-transitory program storage devices for identifying demographic information in an input data file and converting that data into autonomous data of an export entity file. In an embodiment, the received tabular data is sorted based on a lowest number of unique entities of a certain type in the revised data file, common data describing the lowest number of unique entities is extracted, labeled, and stored as an autonomous export entity file. In an embodiment a plurality of autonomous export entities are linked to create a master export entity comprising the plurality of autonomous export entities.

20 Claims, 16 Drawing Sheets

(56)                    References Cited

U.S. PATENT DOCUMENTS

| | | |
|---|---|---|
| 2019/0392075 A1 | 12/2019 | Han et al. |
| 2021/0125089 A1* | 4/2021 | Nickl .................... H04W 12/02 |
| 2021/0174380 A1 | 6/2021 | Vera-Ciro et al. |
| 2023/0273848 A1 | 8/2023 | Vera-Ciro et al. |

* cited by examiner

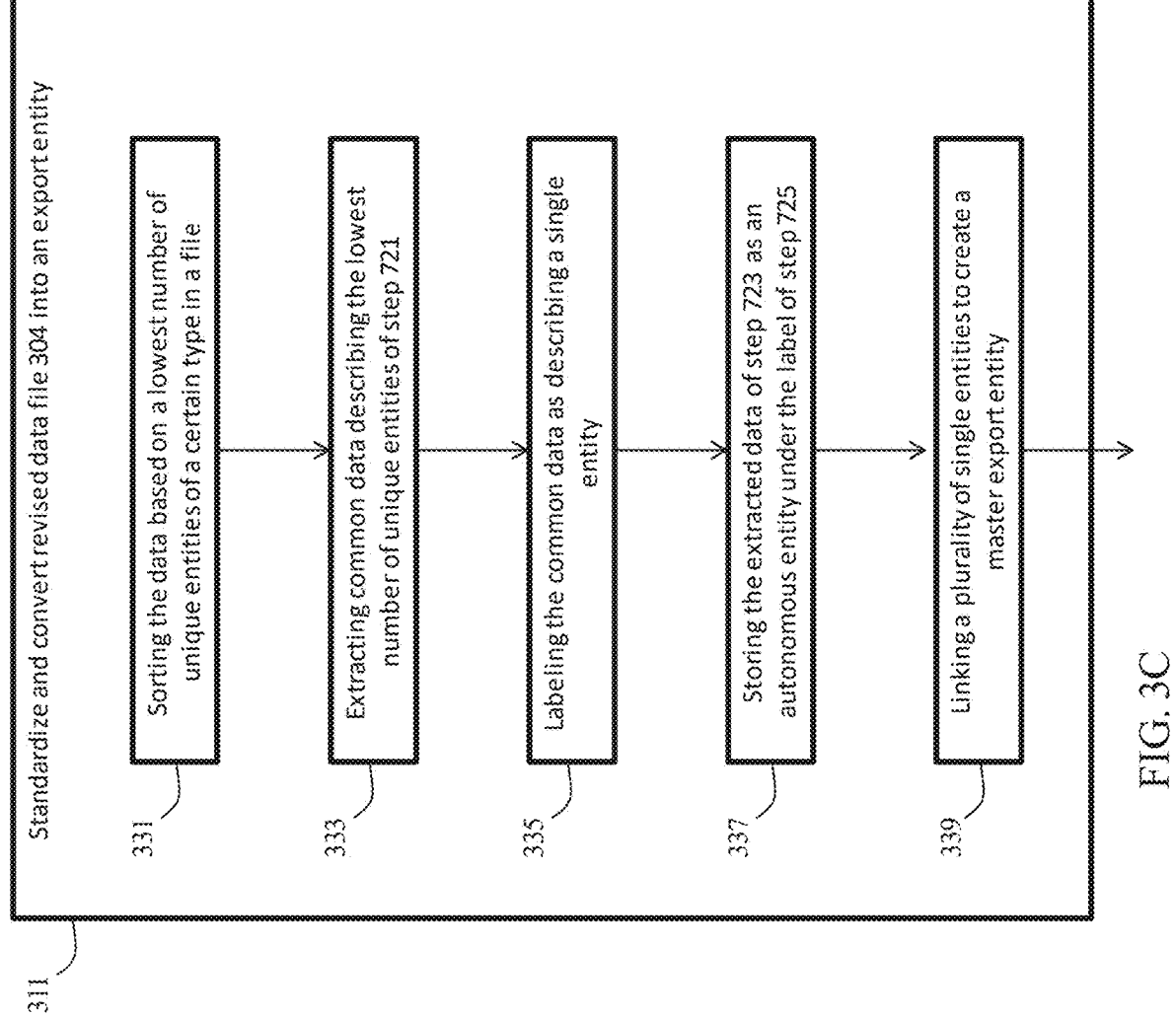

Standardize and convert revised data file 304 into an export entity

311

331 — Sorting the data based on a lowest number of unique entities of a certain type in a file 333 — Extracting common data describing the lowest number of unique entities of step 721

335 — Labeling the common data as describing a single entity

337 — Storing the extracted data of step 723 as an autonomous entity under the label of step 725

339 — Linking a plurality of single entities to create a master export entity

FIG. 3C

| Name | Addrs. | PH# | FX# | Specialty | License No. | Expiration Date |
|---|---|---|---|---|---|---|
| Doe, John | 123 Maple Ave Somehwere, NJ 07005 | (973) 999-1234 | john.doe@doctor.org | IM | 123456 | 12/22/2020 |
| Doe, Jane | 123 Maple Ave Somehwere, NJ )7005 | (973) 999-1234 | jane.doe@doctor.org | Internal Medicine | 123457 | 12/22/2020 |

FIG. 4A

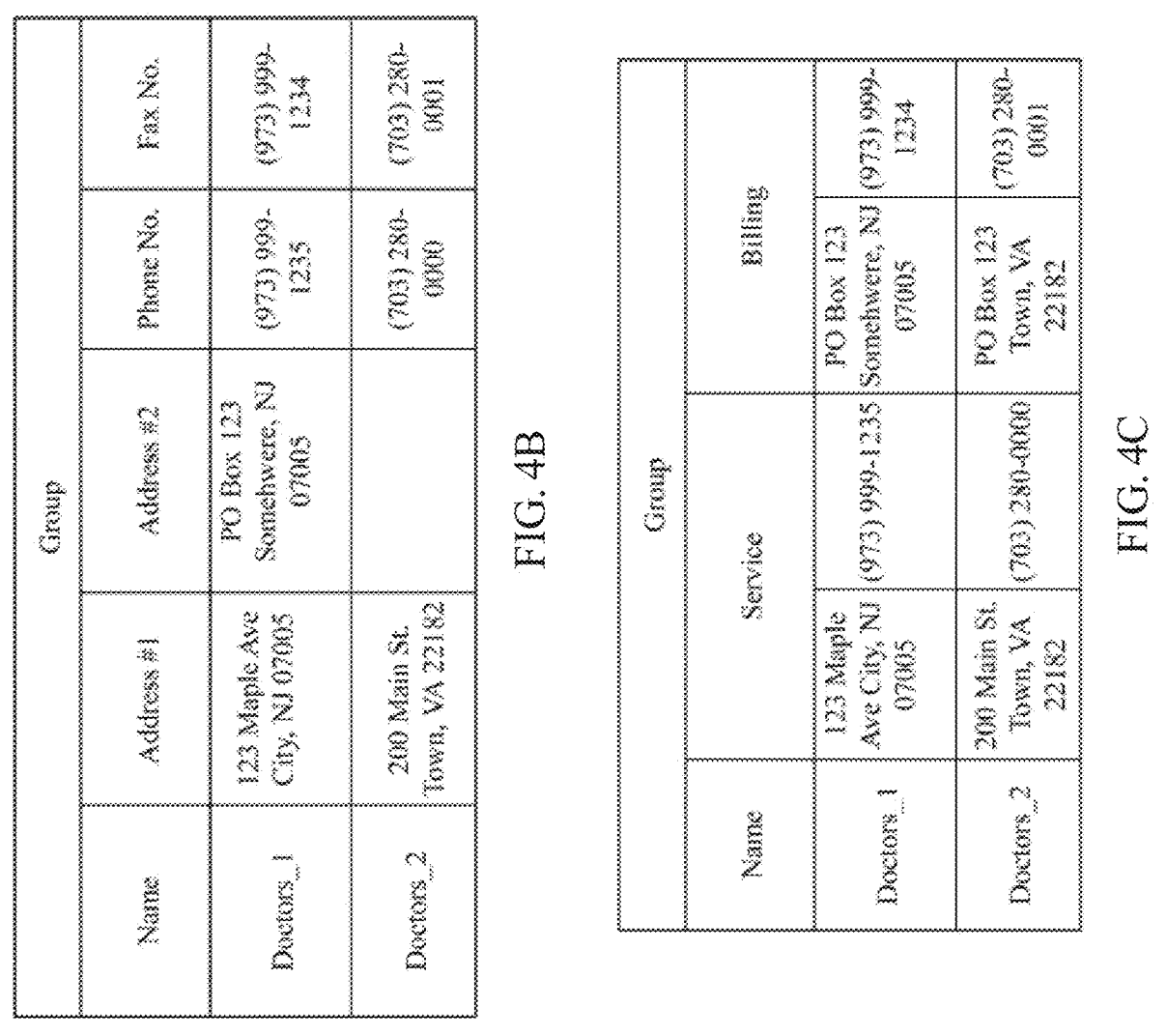

| Group | | | | | |
|---|---|---|---|---|---|
| Name | Address #1 | Address #2 | Phone No. | Fax No. |
| Doctors_1 | 123 Maple Ave City, NJ 07005 | PO Box 123 Somehwere, NJ 07005 | (973) 999-1235 | (973) 999-1234 |
| Doctors_2 | 200 Main St. Town, VA 22182 | | (703) 280-0000 | (703) 280-0001 |

FIG. 4B

| Group | | | |
|---|---|---|---|
| Name | Service | Billing | |
| Doctors_1 | 123 Maple Ave City, NJ 07005 (973) 999-1235 | PO Box 123 Somehwere, NJ 07005 | (973) 999-1234 |
| Doctors_2 | 200 Main St. Town, VA 22182 (703) 280-0000 | PO Box 123 Town, VA 22182 | (703) 280-0001 |

FIG. 4C

| Group Name | | |
|---|---|---|
| Name | Addr | |
| John Doe | 123 Maple Ave Somehwere, NJ 07005 | |
| | Name | Addr |
| | Jane Doe | 125 Maple Ave Somewhere, NJ 07005 |

FIG. 4D

| Name | Addrs. 1 | City 1 | State 1 | Addrs. 2 | City 2 | State 2 |
|---|---|---|---|---|---|---|
| Doe, John | 123 Maple Ave | Somewhere | NJ | 456 Main St. | Somehwere | NY |

FIG. 4E

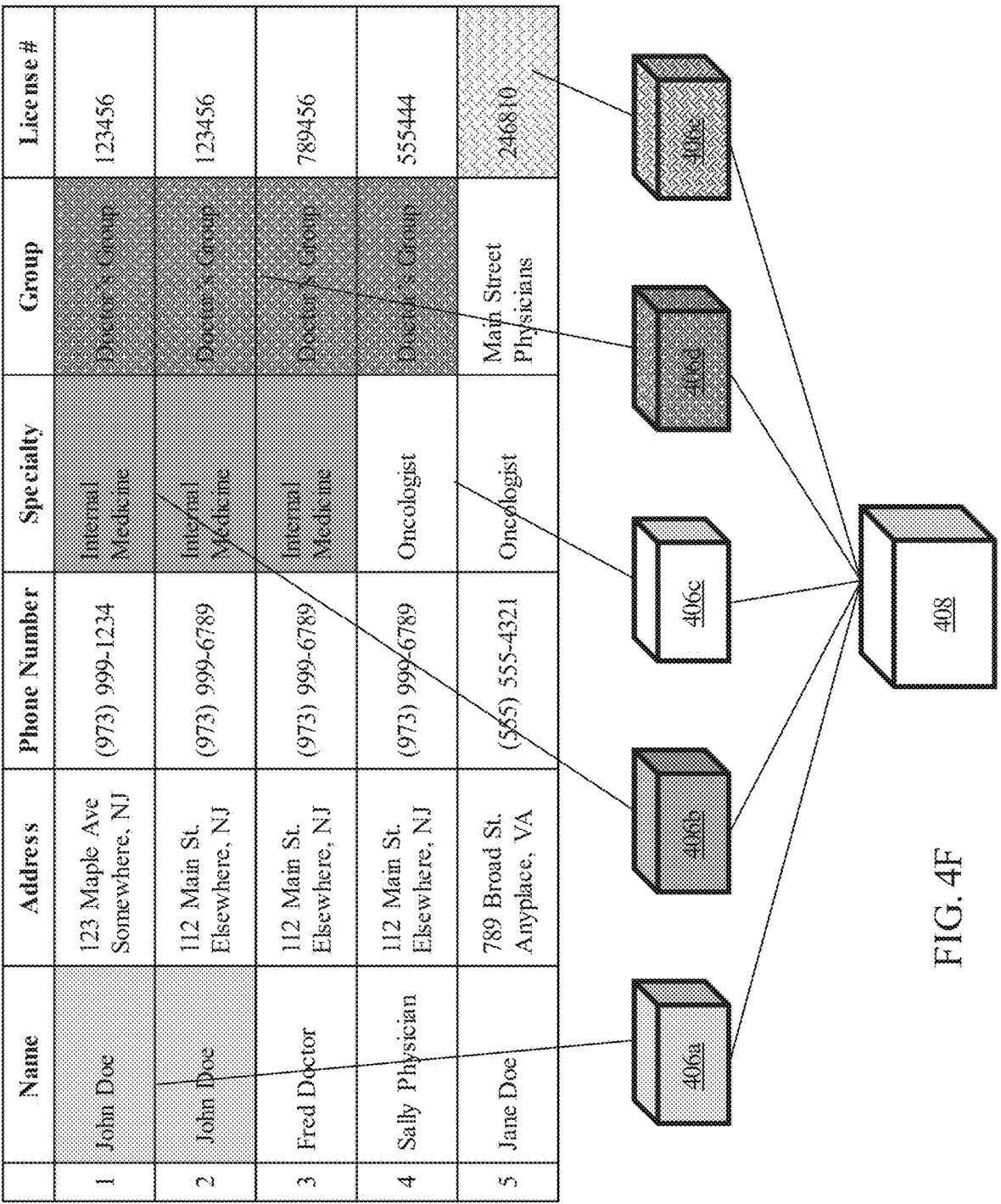

| | Name | Address | Phone Number | Specialty | Group | License # |
|---|---|---|---|---|---|---|
| 1 | John Doe | 123 Maple Ave Somewhere, NJ | (973) 999-1234 | Internal Medicine | Doctor's Group | 123456 |
| 2 | John Doe | 112 Main St. Elsewhere, NJ | (973) 999-6789 | Internal Medicine | Doctor's Group | 123456 |
| 3 | Fred Doctor | 112 Main St. Elsewhere, NJ | (973) 999-6789 | Internal Medicine | Doctor's Group | 789456 |
| 4 | Sally Physician | 112 Main St. Elsewhere, NJ | (973) 999-6789 | Oncologist | Doctor's Group | 555444 |
| 5 | Jane Doe | 789 Broad St. Anyplace, VA | (585) 555-4321 | Oncologist | Main Street Physicians | 246810 |

FIG. 4F

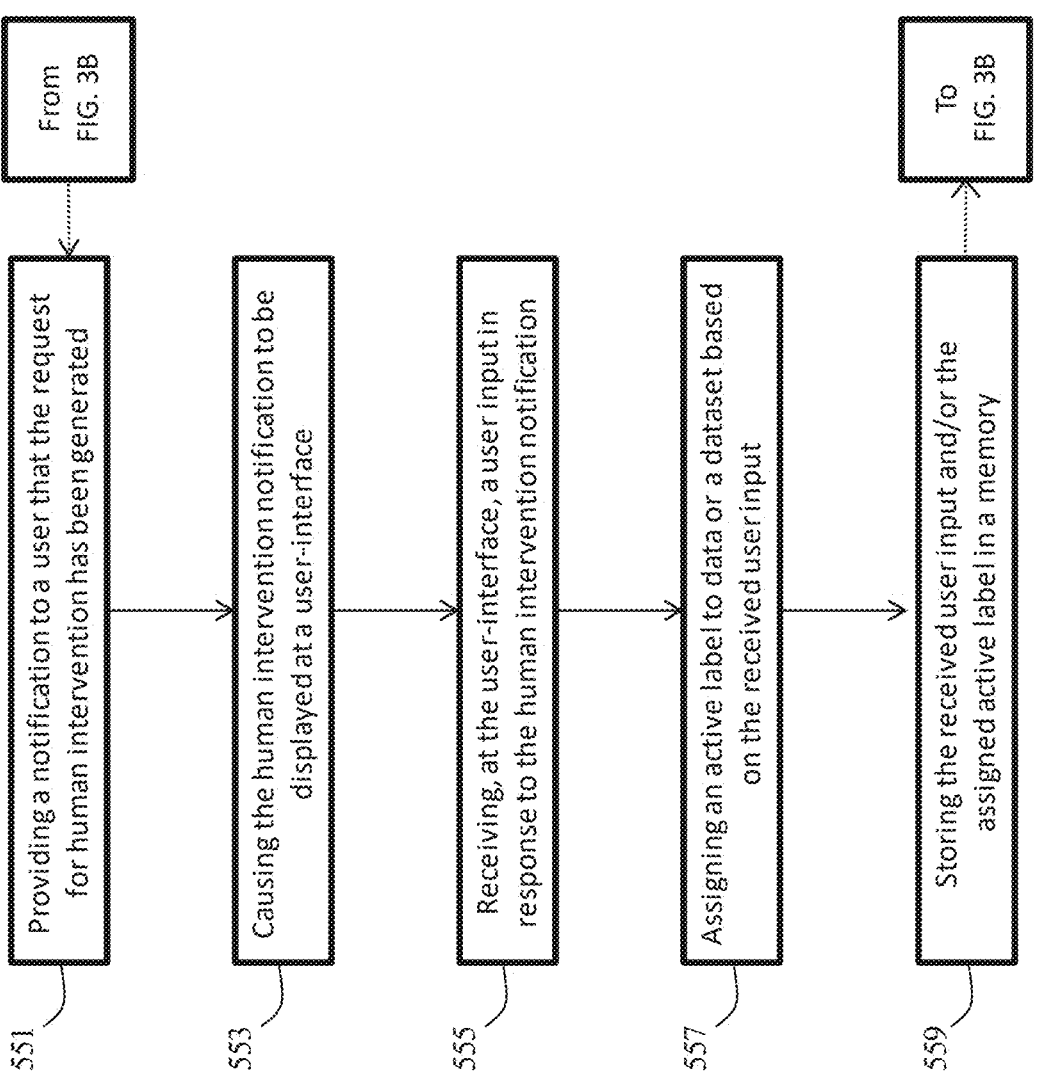

From
FIG. 3B

Providing a notification to a user that the request for human intervention has been generated Causing the human intervention notification to be displayed at a user-interface Receiving, at the user-interface, a user input in response to the human intervention notification Assigning an active label to data or a dataset based on the received user input Storing the received user input and/or the assigned active label in a memory To
FIG. 3B

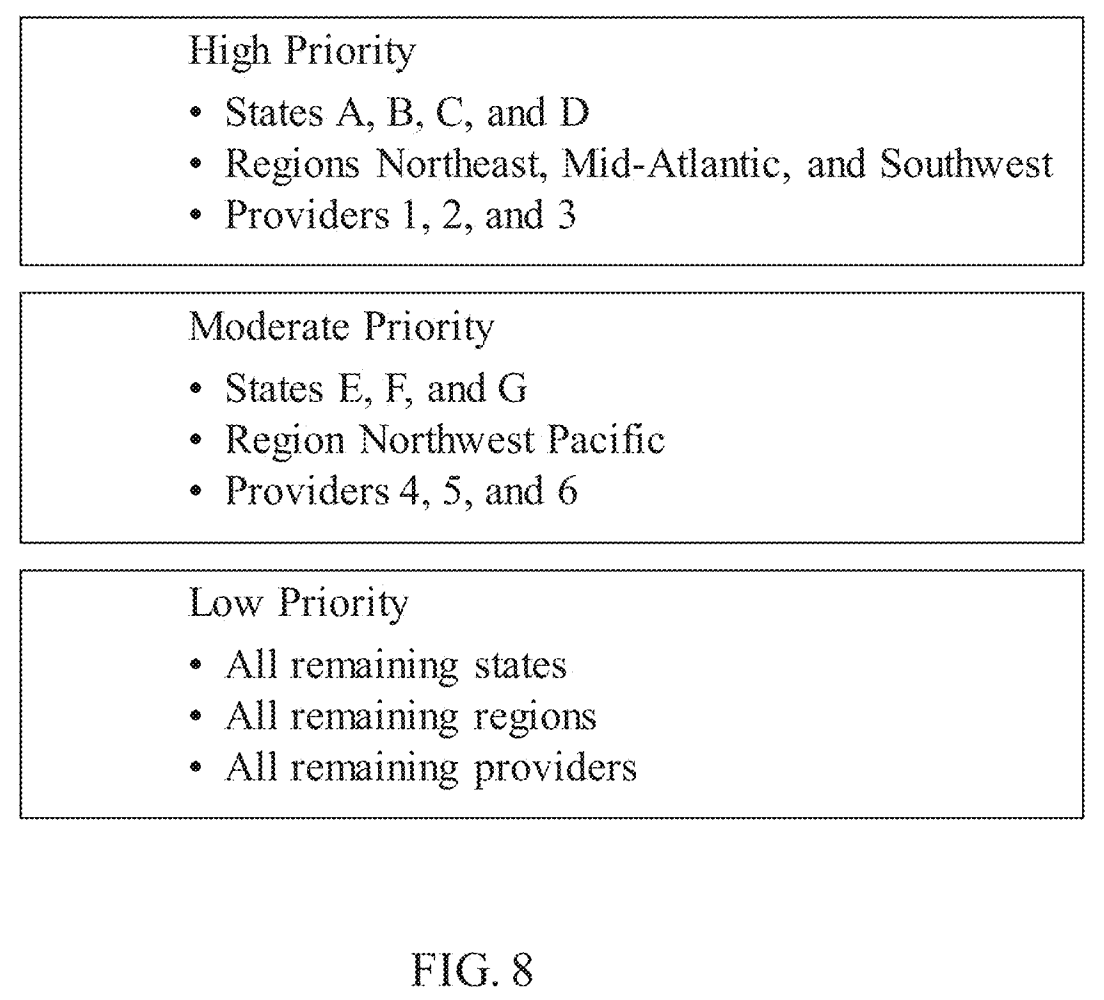

High Priority
- States A, B, C, and D
- Regions Northeast, Mid-Atlantic, and Southwest
- Providers 1, 2, and 3

Moderate Priority
- States E, F, and G
- Region Northwest Pacific
- Providers 4, 5, and 6

Low Priority
- All remaining states
- All remaining regions
- All remaining providers

FIG. 8

| First Name | Last Name | Address | Phone Number | Email Address | Specialty | Licence No. | Expiration Date |
|---|---|---|---|---|---|---|---|
| John | Doe | 123 Maple Ave Somehwere, NJ 07005 | (973) 999-1234 | john.doe@doctor.org | Internal Medicine | 123456 | 12/22/2020 |
| Jane | Doe | 123 Maple Ave Somehwere, NJ 07005 | (973) 999-1234 | jane.doe@doctor.org | Internal Medicine | 123457 | 12/22/2020 |

FIG. 9

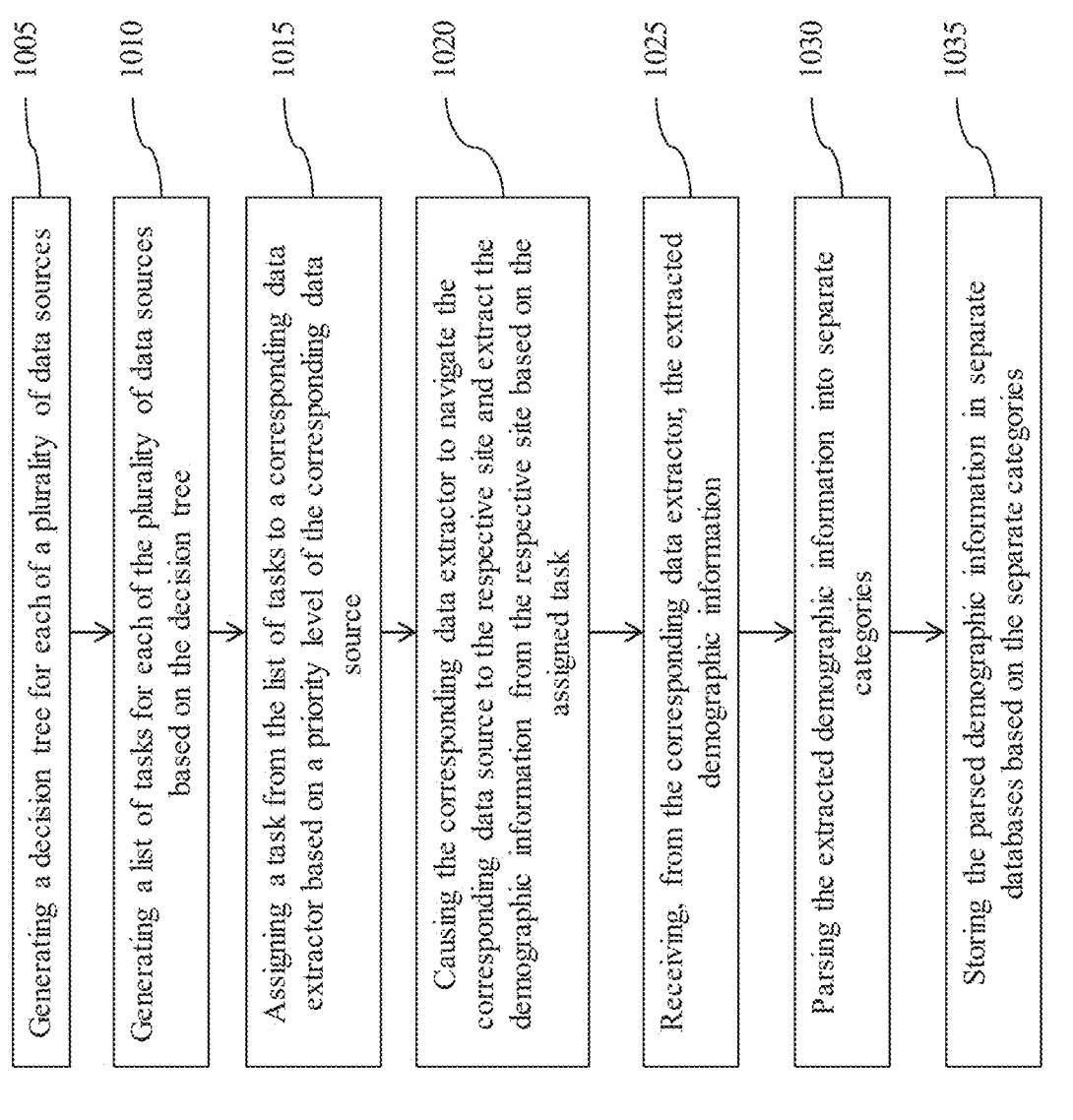

1005 — Generating a decision tree for each of a plurality of data sources

1010 — Generating a list of tasks for each of the plurality of data sources based on the decision tree 1015 — Assigning a task from the list of tasks to a corresponding data extractor based on a priority level of the corresponding data source 1020 — Causing the corresponding data extractor to navigate the corresponding data source to the respective site and extract the demographic information from the respective site based on the assigned task 1025 — Receiving, from the corresponding data extractor, the extracted demographic information 1030 — Parsing the extracted demographic information into separate categories 1035 — Storing the parsed demographic information in separate databases based on the separate categories

CONVERTING TABULAR DEMOGRAPHIC INFORMATION INTO AN EXPORT ENTITY FILE

CROSS-REFERENCE TO RELATED APPLICATION

This application is a continuation of U.S. application Ser. No. 18/114,026, filed on Feb. 24, 2023, which claims priority to U.S. Provisional Application No. 63/268,537, filed on Feb. 25, 2022, the contents of which is incorporated by reference herein in its entirety.

BACKGROUND

Field

This field is generally related to processing information.

Background

As technology advances, an ever-increasing amount of demographic information is becoming digitized. For example, for healthcare providers, demographic information may include, but is not limited, to their name, address, specialties, academic credentials, certifications, and the like. This demographic information may be available from private data sources, such as medical rosters maintained by healthcare providers. Various public data sources, such as medical rosters or websites. Healthcare providers regularly send medical rosters to health insurance companies. These medical rosters include demographic information of each of the healthcare practitioners affiliated with a healthcare provider. This ensures that the health insurance companies have the most current information about the healthcare practitioners affiliated with that specific healthcare provider.

Demographic information may be available from various public data sources as well, such as websites. These websites may retrieve the demographic information from underlying databases, such as state, county, city, or municipality databases, that store the data. For example, states may have licensing boards that maintain lists of all licensed healthcare providers, along with their associated demographic information. In another example, health insurance companies may have public websites listing the healthcare providers, and associated demographic information, in their network. In another example, healthcare providers may themselves set up public websites that list such demographic information about their practices.

Entities, such as health insurance companies, need to have correct and current demographic information about healthcare providers to correctly reimburse them for claimed services, or alternatively, to detect fraudulent insurance claims. Often times the information that is shared between the healthcare providers and the health insurance companies is inaccurate and, in some case, the entire file may be unusable because of corrupt data. Humans often make/create this shared information. Because humans are creative, do not always conform to rules, and seek ways to streamline data entry, the shared information often includes outlier data that may be incorrect, inconsistent, unexpected, or may be unrecognizable by automated processes.

In addition, healthcare providers generally share the demographic information in unique formats, using unique nomenclatures. Thus, the files and information shared by one healthcare provider may be vastly different from the information shared by another healthcare provider. While the uniquely presented data from each healthcare provider may be readily identifiable to a human, automated systems may have difficulty parsing the data and associating the demographic information because of the unique formatting and nomenclatures.

Finally, demographic information is generally shared using files having a tabular format (e.g., spreadsheet), often having complex layouts. However, it is difficult to parse, manipulate, revise, or extract data stored in a tabular format without affecting the integrity of the other data. Tabular data often comprises large amounts of duplicative data and it can become cumbersome to repeatedly process and compute the replicated data. Efforts have been made to consolidate rows based on specific features, but in combining rows, the tabular data loses autonomy and it fails to account for many variables described in specific columns of a given row. Thus, consolidating rows is limited and inefficient.

Thus, systems and methods are needed to improve extracting the demographic information from these data sources and consolidating the demographic information into a validated, autonomous, and up-to-date export entity file while reducing the burden on physicians, healthcare providers, and health insurance providers.

BRIEF DESCRIPTION OF THE DRAWINGS

The accompanying drawings, which are incorporated herein and form part of the specification, illustrate the present disclosure and, together with the description, further serve to explain the principles of the disclosure and enable a person skilled in the relevant art to make and use the disclosure.

FIG. 3C illustrates an exemplary method for standardizing and converting revised data files into export entities according to aspects of the present disclosure.

FIG. 4A-E illustrate example data files received from the one or more data sources, according to aspects of the present disclosure.

FIG. 4F illustrates example data files received from the one or more data sources and a method of generating export entity files, according to aspects of the present disclosure.

FIG. 5 illustrates a method for processing user input according to aspects of the present disclosure.

FIG. 8 illustrates example priority levels assigned to the one or more data sources, according to aspects of the present disclosure.

FIG. 9 illustrates an example report generated by the system for accumulating data from the one or more data sources, according to aspects of the present disclosure.

FIG. 10 illustrates a method of extracting unstructured data from a plurality of data sources, according to aspects of the present disclosure.

The drawing in which an element first appears is typically indicated by the leftmost digit or digits in the corresponding reference number. In the drawings, like reference numbers may indicate identical or functionally similar elements.

DETAILED DESCRIPTION

Figure 1:
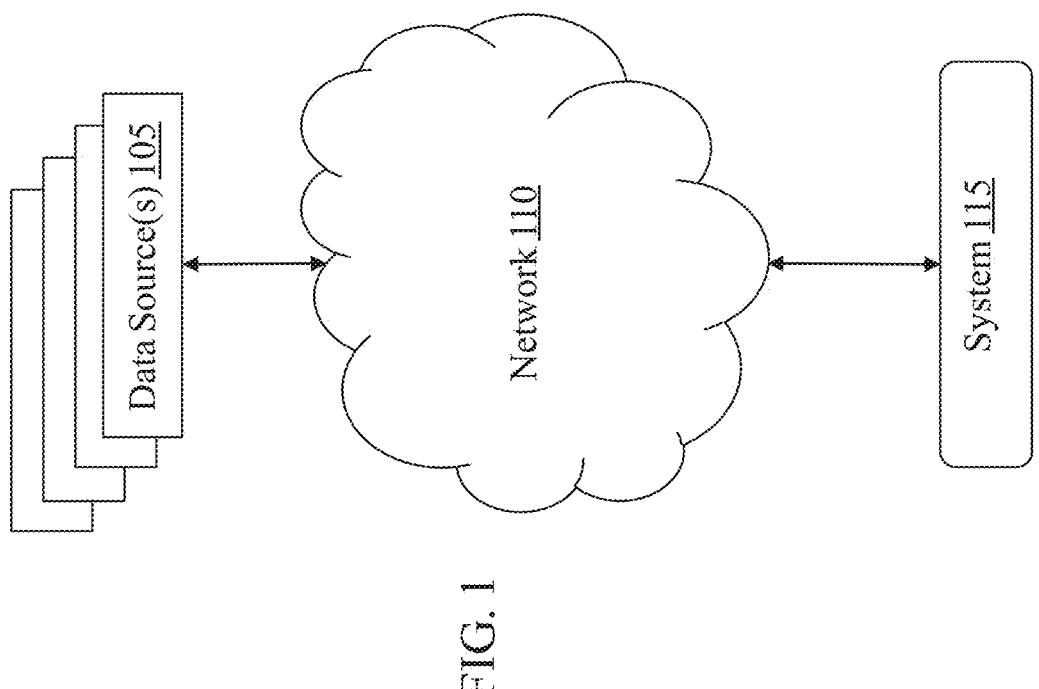
FIG. 1 illustrates a diagram of a network for communications between one or more data sources and a system, according to aspects of the present disclosure.

Embodiments provide ways to review and reformat data files that include inconsistent or mislabeled nomenclatures for one or more fields of a plurality of fields of demographic information or spurious demographic information, which would require weeks per file to review and reformat manually. For example, embodiments may analyze the data file using a machine learning model trained according to other data files to distinguish between each of the plurality of fields of demographic information. The machine learning model may be based on a plurality of machine learning algorithms to identify different types demographic information. For example, analyzing the data file may be based on a combination of one or more of semantic content of the demographic information, a shape of the demographic information, or metadata. In this way, embodiments provide the ability to identify different types of demographic data. Embodiments may also generate a score indicating a probability that each of the plurality of fields of demographic information was identified correctly. Embodiments may also generate a revised data file labeling each of the plurality of fields of demographic information based on the identified type. For example, the revised data file may be formatted based on the requirements of the third-party that provided the original data file. In other words, the revised data file may be fully customizable based on individual requests for the restructured data. The revised data file may be formatted as an export entity that is fully autonomous. For example, a machine learning algorithm may be used to sort tabular data based on a type of entity, extract common data describing a plurality of similar entities, and store the entity as an autonomous exportable entity file. Thus, embodiments provide the ability to effectively and efficiently generate data files in a format that is most useful to the third party.

Furthermore, embodiments provide ways to complete the data review in the presence of a fault condition that might derail, stop, or prevent a plurality of machine learning algorithms from completing its tasks. For example, when receiving a corrupt data file or a data file that has corrupt data, machine learning algorithms and other methods for identifying demographic information shut down in the face of a resulting fault condition. In this manner, the embodiments and aspects described herein improve the efficiency and functionality of a computer because it is able to process data that would otherwise stall, stop, or prevent a data review process from occurring. In embodiments, the fault condition may be presented to, and ultimately resolved by, a human user.

The present disclosure may implement a combination of a plurality of machine learning algorithms and rules, which improves the functionality of the computing device. Namely, the combination of machine learning algorithms and rules avoids overtraining, and thus overcomplicating, the machine learning model, thereby reducing the amount of resources, e.g., processing consumption and memory resources, required to generate reformatted data files. Additionally, in some aspects, the present disclosure may intelligently identify different types of demographic information based on a sampled portion of the data file, rather than the entire data file, which may include hundreds, if not thousands of entries. By identifying the different types of demographic information based on a sampled portion, the present disclosure may further reduce the amount of resources required to generate reformatted data files.

In the detailed description that follows, references to "one embodiment", "an embodiment", "an example embodiment", etc., indicate that the embodiment described may include a particular aspect, feature, structure, or characteristic, but every embodiment may not necessarily include the particular aspect, feature, structure, or characteristic. Moreover, such phrases are not necessarily referring to the same embodiment. Further, when a particular aspect, feature, structure, or characteristic is described in connection with an embodiment, it is submitted that it is within the knowledge of one skilled in the art to effect such aspect, feature, structure, or characteristic in connection with other embodiments whether or not explicitly described.

FIG. 1 is a diagram illustrating a network 100 for communications over a network 110 between one or more data sources 105 and a system 115. In some embodiments, the one or more data sources 105 may be any data source that maintains databases of demographic information of one or more individuals, such, as healthcare providers, including but not limited to, doctors, dentists, physician assistants, nurse practitioners, nurses, or the like. Although the present disclosure describes the individuals as being healthcare providers, it should be understood by those of ordinary skill in the arts that the present disclosure may be implemented accumulating data from any data source. In some embodiments, the data sources 105 may be hosted on a server, such as a host server, a web server, an application server, etc., a data center device, or a similar device, capable of communicating via the network 110.

In some instances, the one or more data sources 105 may include a Center for Medicaid and Medicare (CMS) services data source, a directory data source, a Drug Enforcement Agency (DEA) data source, a public data source, a National Provider Identifier (NPI) data source, a registration data source, and/or a claims data source. The CMS data source may be a data service provided by a government agency. The database may be distributed and different agencies/organizations may be responsible for different data stored in the CMS data source. The CMS data source may also include data on healthcare providers, such as lawfully available demographic information and claims information. The CMS data source may also allow a provider to enroll and update its information in the Medicare Provider Enrollment System and to register and assist in the Medicare and Medicaid Electronic Health Records (EHR) Incentive Programs.

The directory data source may be a directory of healthcare providers. In one example, the directory data source may be a proprietary directory that matches healthcare providers with demographic and behavioral attributes that a particular client believes to be true. The directory data source may, for example, belong to an insurance company or a health system, and can only be accessed and utilized securely with the company's consent.

The DEA data source may be a registration database maintained by a government agency such as the DEA. The DEA may maintain a database of healthcare providers, including physicians, optometrists, pharmacists, dentists, or veterinarians, who are allowed to prescribe or dispense medication. The DEA data source may match a healthcare provider with a DEA number. In addition, the DEA data source may include demographic information about health-care providers.

The public data source may be a public data source, perhaps a web-based data source such as an online review system. These data sources may include demographic information about healthcare providers, area of specialty, and behavioral information such as crowd sourced reviews.

The NPI data source may be a data source matching a healthcare provider to an NPI. The NPI is a Health Insurance Portability and Accountability Act (HIPAA) Administrative Simplification Standard. The NPI is a unique identification number for covered health care providers. Covered health care providers and all health plans and health care clearing-houses must use the NPIs in the administrative and financial transactions adopted under HIPAA. The NPI is a 10-position, intelligence-free numeric identifier (10-digit number). This means that the numbers do not carry other information about healthcare providers, such as the state in which they live or their medical specialty. NPI data source may also include demographic information about a healthcare provider.

The registration data source may include state licensing information. For example, a healthcare provider, such as a physician, may need to register with a state licensing board. The state licensing board may provide the registration data source information about the healthcare provider, such as demographic information and areas of specialty, including board certifications.

The claims data source may be a data source with insurance claims information. Like the directory data source, the claims data source may be a proprietary database. Insurance claims may specify information necessary for insurance reimbursement. For example, claims information may include information on the healthcare provider, the services performed, and perhaps the amount claimed. The services performed may be described using a standardized code system, such as ICD-9. The information on the healthcare provider could include demographic information.

The one or more data sources 105 may receive data files from any number of origins, e.g., multiple practice groups, other ones of the plurality of data sources 105, etc. For example, the one or more data sources 105 may receive responses to requests for demographic information from, for example, medical practice groups, hospitals, or the like. This information may be entered by an administrator, and as such, the data file may include inconsistent or mislabeled nomen-clatures for one or more fields of a plurality of fields of demographic information or it may include spurious demo-graphic information. As another example, the one or more data sources 105 may acquire another entity that utilizes different nomenclatures for one or more fields of the plu-rality of fields. In some implementations, one or more of the plurality of data sources 105 may transmit a data file containing the plurality of fields of demographic information to the system 115.

The network 110 may include one or more wired and/or wireless networks. For example, the network 110 may include a cellular network (e.g., a long-term evolution (LTE) network, a code division multiple access (CDMA) network, a 3G network, a 4G network, a 5G network, or another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

Figure 2:
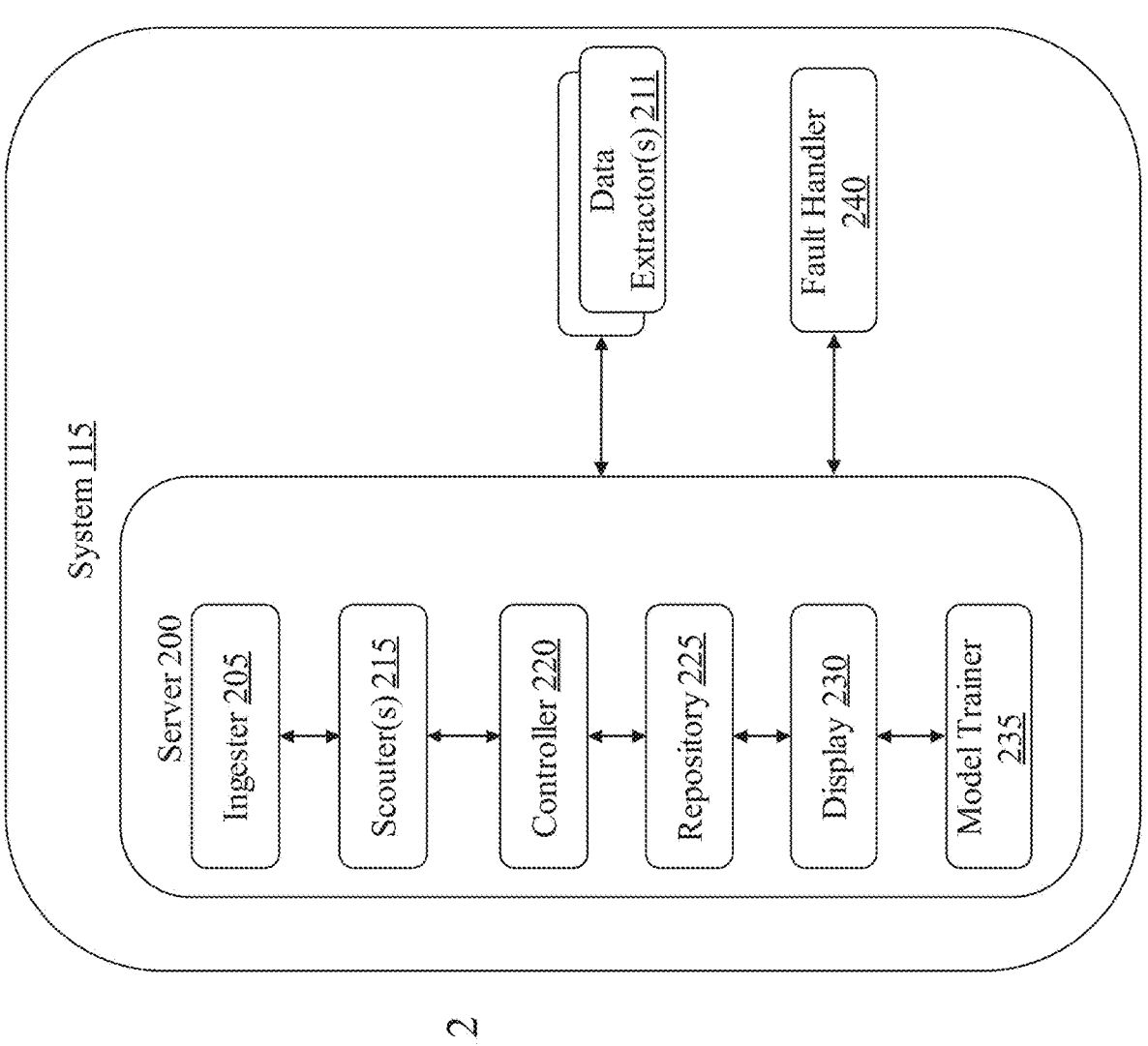
FIG. 2 illustrates a diagram of a system for reviewing and reformatting data files from the one or more data sources, according to aspects of the present disclosure.

To accumulate and store the demographic information from the data sources 105, the system 115 may include various exemplary components as illustrated in FIG. 2. It should be noted that certain embodiments described herein may only use a subset of the illustrated components while other embodiments may include additional components to perform a prescribed task or function.

FIG. 2 depicts system 115 which, in this embodiment, includes a server 200 having one or more scouters 215, an ingester 205, a controller 220, a repository 225, a display 230, and a model trainer 235. System 115 may further include one or more data extractors 211 and a fault handler 240. In some embodiments, fault handler 240 may be located in server 200. The features and functionalities of the foregoing system 115 components are discussed with respect to the methods illustrated in FIGS. 3A-D—which illustrate aspects of the methods and system described herein.

Figures 3A, 3B:
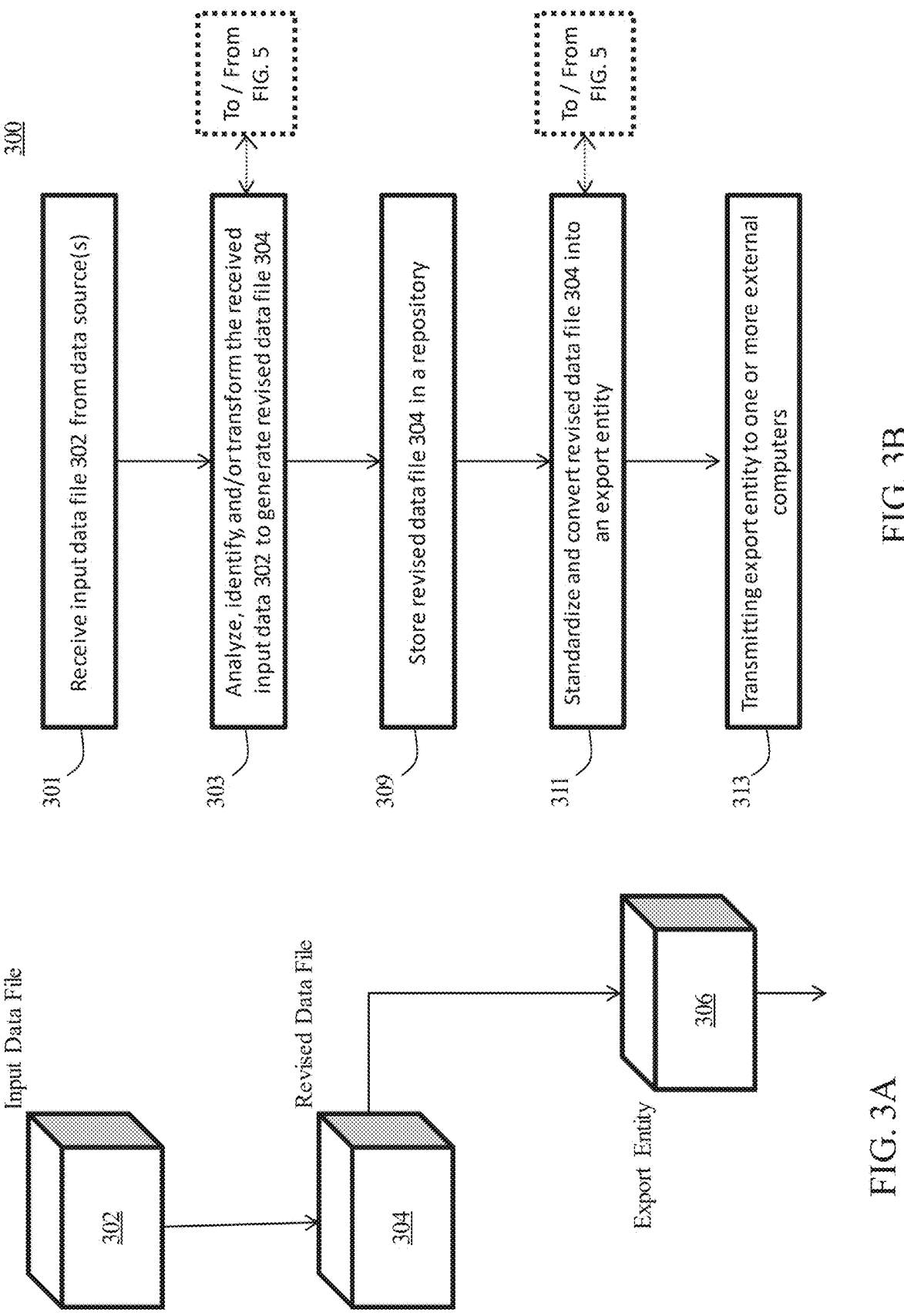
FIGS. 3A-B illustrates a diagram and exemplary method for transforming data and converting the transformed data into an export entity according to aspects of the present disclosure.

For example, FIGS. 3A-B, illustrate an exemplary method 300 for transforming data and converting the transformed data into an export entity. For example, the figures illustrate receiving the input data file 302 from the data sources 105 and, using ingester 205, analyzing and transforming the received input data file 302 into a revised data file 304. The revised data file 304 may be stored in repository 225 in the form of input data file 302, which is generally in tabular data form such as a spreadsheet, or as a new file type. The method further includes converting stored revised data file 304 into an export entity such as, for example, a JSON file or another language-independent file format, and transmitting the export entity to a remoted computer over a network. Additional details of this method are included below.

At step 301, the system receives input data file 302 from the data sources 105. At step 303, the system analyzes and transforms the received input data file 302 into a revised data file 304.

In some embodiments, step 303 includes analyzing the received input data file 302 to determine whether the file is corrupt or whether any other fault condition or exception conditions exist, at the file level, that may cause the system and method to stall or otherwise fail to perform its intended functionality. Fault handler 240 (of FIG. 2) is recruited when input data file 302 is determined to be corrupt and/or containing another fault condition.

Depending on the nature of the fault condition, the fault handler 240 may either attempt to fix the corrupt file or remove the data causing the fault condition from the input data file and resume/begin processing the input data. In some embodiments, fault handler 240 may request human inter-vention (as described in FIG. 5, below). In such embodi-ments, the system may continue processing the data regard-less of whether human input has been received because the system can bypass or remove the corrupt data until the human input is received, thereby keeping the method fault tolerant. A person of ordinary skill would appreciate this aspect of the invention for its fault-tolerant characteristics in the face of known errors that would otherwise prevent the method from operating. This type of fault tolerance not only improves the function of a computer by continuing to operate in the face of otherwise debilitating errors, but it also saves time and money.

Additional exemplary methods for analyzing and trans-forming the received input data 302 at step 303 are described herein. For example, in some embodiments, ingester 205 may analyze input data file 302 using a machine learning model trained according to other data files to distinguish between each of the plurality of fields of demographic information. In some embodiments, model trainer 235 may train the machine learning model using a number of Monte Carlo training sets having sample data files. That is, model trainer 235 may use a sample set generated by humans identifying demographic information in a data file. In some embodiments, the machine learning model may be based on a plurality of machine learning algorithms to identify different types of demographic information. In some embodiments, the plurality of machine learning algorithms may be supervised machine learning algorithms including, but are not limited to, support vector machines, linear regression, logistic regression, naive Bayes, linear discriminant analysis, decision trees, k-nearest neighbor algorithm, neural networks, and similarity learning. It should be understood by those of ordinary skill in the art that these are merely examples of supervised machine learning algorithms and that other supervised machine learning algorithms may be used in accordance with aspects of the present disclosure.

As an example of a step 303 analysis, ingester 205 may analyze the data file by analyzing semantic content of each of the plurality of fields of demographic information to identify the different types of demographic information. For example, ingester 205 may identify semantic content, such as a state name or state abbreviation, which indicates that the demographic information is likely an address, rather than, for example, a phone number or facsimile number. Similarly, ingester 205 may identify semantic content, such as street names (e.g., Avenue, Road, Street, Lane, etc.) and/or their associated abbreviations (e.g., Ave., Rd. St. Ln., etc.), which would likewise also indicate that the demographic information is an address. Even further, ingester 205 may identify semantic content, such as state names (or country names) and/or their associated abbreviations, which would likewise also indicate that the demographic information is an address. In some embodiments, ingester 205 may also be able to identify a billing address based on the semantic content. For example, the semantic content may include, for example, a PO Box number, which would indicate that the content is a billing address, rather than a service address. In yet another example, ingester 205 may identify the semantic content, such as a hyperlink, which may indicate that the demographic information is an email address. It should be understood by those of ordinary skill in the art that these are merely examples of semantic content that may be identified, and that other types of semantic content are contemplated in accordance with aspects of the present disclosure.

As another example of a step 303 analysis, ingester 205 may analyze the data file by analyzing a shape of each of the plurality of fields of demographic information to identify the different types of demographic information. For example, ingester 205 may analyze the demographic information to identify the number of characters, the type of the characters (e.g., numeric versus letter characters), the number of non-alphanumeric characters (e.g., spaces, commas, periods, or the like), and an overall arrangement of the alphanumeric characters and non-alphanumeric characters. For example, the shape of the demographic information may be "XXX[comma][space]XXX" or "XXX[comma][space]XXX[space]X[period]", with each X representing a letter character, which are common formats identifying names. In another example, the shape of the demographic information may be ###XXX[space]XXX [space]XXX[comma]XX [space] ##### (or #####–####), with each # representing a numeric character and each X representing a letter character, which is a common format of an address. However, some data files may use a full state name, rather than the two letter abbreviation for the state, and as such, ingester 205 may identify the state within an address based on the semantic content, as discussed herein. In yet another example, ingester 205 may identify the shape of the demographic information, such as XXX@XXX[period]XXXX, which indicates that the demographic information is an email address. It should be understood by those of ordinary skill in the arts that these are merely examples of shapes of demographic content that may be identified, and that other types of shapes of demographic content are contemplated in accordance with aspects of the present disclosure.

As yet another example of a step 303 analysis, ingester 205 may analyze the data file by analyzing metadata of each of the plurality of fields of demographic information to identify the different types of demographic information. For example, the metadata may include each nomenclature of the headings. In some instances, the semantic content and shapes of the demographic information may be similar. For example, phone numbers and facsimile numbers may have similar semantic content and shapes. In another example, service addresses and billing addresses may have similar semantic content and shapes. To differentiate between demographic information having similar semantic content and shapes, ingester 205 may analyze the metadata of the headings (or subheadings). For example, ingester 205 may identify common nomenclatures used for the different types of demographic information. For example, common nomenclatures for phone numbers may include, but are not limited to, "Phone No.," "Phone Number," "P:," "PH No.," or the like, whereas common nomenclatures for facsimile numbers may include, but are not limited to, "Fax No.," "Fax Number," "F:," "FX No.," or the like. Likewise, common nomenclatures for service addresses may include the terms, for example, "Service," "Serv.," or the like, or the service address may be listed only as "Address" or some variation thereof, whereas the billing address may be specifically identified as such. Furthermore, ingester 205 may analyze layered headings, as illustrated in the examples shown in FIGS. 4A-F. For example, ingester 205 may analyze the headings "Author Name" and "Date Generated," and determine that these fields are merely extraneous metadata and/or superfluous information that should be removed when reformatting the data file. As another example, using the data file shown in FIG. 4B, ingester 205 may analyze the primary heading and subheadings, and determine that the demographic information provided below the primary heading is related to a practice group, i.e., a group name ("Name"), group service address ("Address #1"), group billing address ("Address #2), group phone number ("Phone No."), and group facsimile number ("Fax No."). In yet another example, using the data file shown in FIG. 4C, ingester 205 may analyze the primary heading and subheadings, and determine that the demographic information provided below the primary heading is related to a practice group, i.e., a group name, however the remaining subheadings are "Service" and "Billing," and ingester 205 may determine that the demographic information provided under these subheadings are a billing address, billing phone number, service address, and service phone, respectively.

In some embodiments, the machine learning model may also be trained on respective rules for common types of demographic information. For example, the rules may include a rule that a five digit number or a five digit number followed by a hyphen and another four digit number is a zip code, as these are the only available formats for zip codes. As another example, an NPI may be formatted as a ten digit number with the first digit being a "1," and as such, the rules may include a rule indicating that any ten digit number commencing with a "1" is an NPI. In a further example, the rules may include a rule for determining responses to binary pieces of demographic information, e.g., whether a health-care provider is accepting new patients—"Yes"/"Y" or "No"/"N." By using rules for common types of demographic information, the present disclosure avoids overtraining, and thus overcomplicating, the machine learning model and also improves efficiency of the machine learning model. In some embodiments, these rules may be defined as regular expres-sions, however it should be understood by those ordinary skill in the arts that other types of rules may be used.

In some embodiments of a step 303 analysis, ingester 205 may analyze the inter-columnar relationship between mul-tiple columns. For example, as illustrated in FIG. 4D, the data file includes alternating headings of "Name" and "Addr." After reviewing the semantic content, shape, and metadata of the rows under each column, ingester 205 may determine that the respective types of demographic infor-mation are names and addresses. Furthermore, by analyzing the inter-columnar relationship between multiple columns, ingester 205 may determine that the alternating headings should be grouped as pairs, e.g., a healthcare provider name and their associated address. As another example illustrated in FIG. 4E, the data file may include multiple addresses for a single healthcare provider, i.e., "Addrs. 1," "City 1," "State 1," as well as "Addrs. 2," "City 2," "State 2." In this instance, ingester 205 may determine that each address is associated with the same healthcare provider, and separate each address into separate entries, e.g., separate row of information, in a revised data file, while still associating the addresses with the same healthcare provider.

Ingester 205 may also generate a score indicating a probability that each of the plurality of fields of demo-graphic information was identified correctly. For example, ingester 205 may generate a baseline score for each of the plurality of fields of demographic information, which may then be adjusted. For example, ingester 205 may increase the scores for demographic information having well-known semantic content and/or shapes, e.g., zip codes and NPIs. Additionally, ingester 205 may increase or decrease the score based on whether the heading correctly identifies the associated demographic information, e.g., whether the head-ing correctly identifies "NPIs." For example, the score may be decreased when the heading and the content do not match, whereas the score may be increased when the head-ing and content match. In some embodiments, ingester 205 may increase the score based on whether demographic information having similar semantic content and/or shapes have been detected. For example, ingester 205 increases the score for a telephone number or address if only a single piece of demographic information having the given semantic content and/or shape is identified. However, in the event two or more identified fields of demographic information having the same semantic content and/or shape are identified (e.g., a phone number and a facsimile number or a service address and a billing address), ingester 205 may decrease the score for both of the two or more identified fields of demographic information, and these identified fields may have the same score.

Furthermore, in some situations, ingester 205 may gen-erate an alert notifying an administrator of the two or more identified fields of demographic information having the same semantic content and/or shape, such that the admin-istrator may provide input to resolve the conflict (as described in FIG. 5, below). In such embodiments, the system may continue processing the data regardless of whether human input is required and/or has been received because the system can bypass or remove the corrupt data until the human input is received, thereby keeping the method fault tolerant. A person of ordinary skill would appreciate this aspect of the invention for its fault-tolerant characteristics in the face of conflicting data errors that would otherwise prevent the method from operating or might cause the method to operate in an infinite loop. This type of fault tolerance not only improves the function of a computer by continuing to operate in the face of otherwise debilitating errors, but it also saves time and money.

In some embodiments of a step 303 analysis, ingester 205 may resolve this conflict by applying additional processing to distinguish between the two or more identified fields of demographic information. For example, in some embodi-ments, ingester 205 may cross-check at least one of the plurality of fields of demographic information against known demographic information stored in, for example, repository 225 (of FIG. 2). For example, ingester 205 may cross-check an identified phone number and an identified facsimile number against known phone numbers and fac-simile numbers to verify which is the phone number and which is the facsimile number. In some embodiments, ingester 205 may sequentially check the digits of the phone and facsimile numbers until ingester 205 determines that one of the two is a phone number. In some instances, only one of the two identified fields of demographic information may be known, e.g., the phone number, and ingester 205 may identify one of the two or more identified fields of demo-graphic information, accordingly, with the remaining field of demographic information being identified as the most rea-sonable alternative (e.g., the facsimile number). Similarly, ingester 205 may cross-check other pieces of demographic information, such as the NPI, service addresses, and billing addresses. It should be understood by those of ordinary skill in the arts that these are merely examples of the types of demographic information that may be cross-checked, and that other types of demographic information may be cross-checked in accordance with aspects of the present disclo-sure.

Additionally, at step 303 ingester 205 may identify incor-rect information and, in some instances, update the incorrect information. For example, as illustrated in FIG. 4A, the zip code in the address associated with "Jane Doe" included a typographical error, and to fix this error, ingester 205 may query the repository 225 to identify a correct zip. Addition-ally, or alternatively, ingester 205 may compare the incorrect zip code to other zip codes of the data file, e.g., the zip code associated with "John Doe," as illustrated in FIG. 4A. As the addresses of "Jane Doe" and "John Doe" have the same street address, city, and state, ingester 205 may determine the zip code associated with "John Doe" is the correct zip code and update the zip code for "Jane Doe" accordingly. Additionally, ingester 205 may determine whether identified information is correct by cross-checking, for example, iden-tified phone numbers against known phone numbers. In some instances, the cross-checking may confirm that the identified numbers are indeed phone numbers. In other instances, the cross-checking may determine that the iden-tified phone numbers were incorrectly labeled in input data file 304, and in fact, are facsimile numbers, rather than phone numbers.

In some embodiments of a step 303 analysis and trans-formation, ingester 205 may analyze a limited number of rows of demographic information in input data file 302 (i.e., less than the full number of rows in the data file) to improve the overall efficiency of ingester 205. For example, after analyzing the semantic content, shape, and metadata of a number of rows, ingester 205 may be able to identify the type of demographic information of each of the plurality of fields of demographic information, and assume that all remaining rows that have not been analyzed are the identified type of demographic information. Furthermore, ingester 205 may transform the data by generating a revised data file in smaller segments of rows, rather than the entire data file, which may require substantial amounts of resources, e.g., processing consumption and memory resources. By assuming the type of demographic information of the remaining rows, ingester 205 reduces the overall amount of resources used and improves the efficiency of the system 115.

Once the plurality of fields of demographic information have been analyzed, identified, and corrected, as needed, ingester 205 may transform the data by generating a revised data file labeling each of the plurality of fields of demographic information based on the identified type by transforming the data. In some embodiments, ingester 205 may generate a revised data file having a format that is customized according to a request from data source 105. For example, the requested format may be a format that is consistent with preexisting data files of data source 105. As another example, the requested format may be an entirely new format. For example, data source 105 may request that the demographic information be separated into "F_Name," "L_Name," "Street Address," "City," "State," and "Zip Code." To achieve this, ingester 205 may identify fields for the requested format and parse through the identified types of demographic information to determine which demographic information belongs in which field of the requested format. That is, for example, when ingester 205 has identified the demographic information as being "Last Name, First Name" or "Full Name," ingester 205 may parse the demographic information and separate it into different fields in the revised data file, i.e., "First Name" and "Last name." That is, the ingester may generate new columns by separating a column of a single type of demographic information (e.g., "Full Name") into different separate columns parsing the single type of demographic information into separate subcomponents (e.g., "First Name" and "Last Name" as separate columns). Likewise, ingester 205 may generate a new set of columns by combining separate columns of information (e.g., "First Name" and "Last Name") into a single column (e.g., "Full Name"). It should be understood by those of ordinary skill in the arts that this is merely an example, and that ingester 205 may parse other types of demographic information in accordance with aspects of the present disclosure. In further embodiments, ingester 205 may separate a single incoming data file into any number of revised data files.

In some instances, a given piece of demographic information may not match what ingester 205 identified as the type of demographic information. For example, ingester 205 may identify one of the plurality of fields of demographic information as being NPIs (National Provider Indentifiers), but one entry may not match the known format for an NPI. In such circumstances, ingester 205 may pass through the mismatching demographic information untouched, render the value null, or insert special characters flagging the particular entry. Alternatively, in some embodiments the mismatching demographic information may trigger a fault condition. Depending on the nature of the fault condition, the fault handler 240 may either attempt to fix the mismatching demographic information or remove the mismatching demographic information from the input data file and resume/begin processing the input data file. In some embodiments, fault handler 240 will require human intervention (as described in FIG. 5, below). In such embodiments, ingester 205 may generate an alert notifying an administrator of the mismatching demographic information, such that the administrator may provide input to resolve the discrepancy. Furthermore, the system may continue processing the data regardless of whether human input has been received because the system can bypass or remove the mismatching demographic information until the human input is received, thereby keeping the method fault tolerant.

In some embodiments, ingester 205 may determine additional information based on the identified demographic information. For example, using the address of the identified address, ingester 205 may determine the geolocation or coordinates of the healthcare provider. As another example, ingester 205 may supplement a missing zip code based on a known street address, city, and state. Ingester 205 may include such additional information in the revised data file upon request.

At step 309, as explained above, when ingester 205 completes the prescribed analysis and transformation, ingester 205 may store the revised data file in the repository 225. The resulting revised data file 304 may be stored in the repository in tabular data form. Alternatively, revised data file 304 may be stored in a format that is customized according to a request from data source 105. For example, the requested format may be a format that is consistent with preexisting data files of data source 105 or it may be an entirely new format.

In some embodiments, the revised data may be stored in the repository 225 for a specified period of time, as long as input data file 302 is being processed, and/or until export entity 306 is transmitted. In some embodiments, the revised data stored in repository 225 is not used to train one or more machine learning models, rather, the stored revised data is cleared, removed, or deleted after a period of time. For example, in an embodiment, the stored revised data may be cleared, removed, or deleted before, during, or after export entity 306 is prepared. In an embodiment, the revised data may be used to analyze future input data files received from the same data source 105. In some embodiments, the stored revised data may be used as an optimus file for a specific client (as described in FIGS. 6B-D, below).

After the system has analyzed, identified, and transformed the data of step 303 and thereby generated revised data file 304, the data is standardized and converted into export entities. That is, at step 311 (and further in FIG. 3C described below), the system standardizes or converts the revised data file 304 into an export entity. As used herein, an entity may include or describe a person, business, practice, employer, address, phone number, or any other demographic data consistent with the embodiments disclosed herein. This process includes transforming the tabular semantic data of the revised data file 304 into autonomous entity container files associated with each unique entity.

In some embodiments, step 311 standardizing and converting may include, for example, sorting the data according to the detected columns to find unique entities, extracting common data describing the lowest number of unique entities, labeling the common data as describing a single entity, storing the extracted data, and/or linking multiple entities. Aspects of step 311 are further described with respect to FIG. 3C, below.

As illustrated at step 331, standardizing and sorting data may include sorting data based on a lowest number of unique entities of a certain type in a file. This step is further exemplified in FIG. 4F which illustrates how some export entities may be sorted based on a lowest number of unique entities of a certain type in the revised data file.

For example, export entity 406a is sorted based on data describing John Doe. Export entities 406b-c are sorted based on data describing medical practitioners having the same specialty—export entity 406b describes medical practitioners specializing in internal medicine whereas export entity 406c describes doctors specializing in oncology. Export entity 406c is sorted based on a group of medical practitioners and 406e is sorted based on data describing a single unique license number. While not shown here, each unique entity may be sorted to its own export entity. In other words, every cell in the exemplary tabular data may be sorted into a unique export entity.

While the export entities depicted in FIG. 4F are sorted based on unique entities describing data found in 1-4 rows of data, in additional embodiments export entities may describe any number of rows of data, including the entire revised data file, so long as the data describes a common unique entity or any entity as defined by a user.

In some embodiments, the data may be sorted at step 331 (of FIG. 3C) based on a plurality of characteristics. In other words, the data may be sorted based on a lowest number of unique entities of multiple data types. For example, again using the data illustrated in FIG. 4F, the data may be sorted based on Phone Number and Group, which would yield an export entity describing the data of rows 1-3. In additional embodiments, other data-type combinations may be used, including more than two data types.

The data sorting of step 331 may be limited to specific data types or columns. In other words, a user may indicate that only a subset of columns should be sorted. For example, a user may limit the sorting feature to sorting a practice group only. In such an embodiment, the system would have only sorted the data related to a specific export entity, e.g., export entity 406d. This selective-sorting aspect may further improve the efficiency of the computer because selecting a subset of the data to be sorted would reduce the amount of computing (i.e., improving efficiency) while delivering user-selected data.

Step 333 of FIG. 3C, the method of standardizing and converting the data into an export entity includes extracting common data describing the lowest number of unique entities of step 331. As explained above, data files are often received in tabular semantic data form, such as a spreadsheet. In such embodiments, extracting common data comprises converting the extracted tabular data into a JSON file format or into another language-independent format. In such JSON or language-independent format files, the resulting data is independent and/or autonomous. As used herein, autonomous means the generated export entities can be manipulated, referenced, extracted, and/or exported without affecting the integrity of the other data stored in the revised data file and/or other export entities. This is yet another example of how the methods described herein improve data processing technology and computer functionality. In legacy systems, data analysis is primarily performed using tabular data and in such systems it is extremely difficult to manipulate the data without negatively affecting other portions of the spreadsheet. Those skilled in the art would appreciate how difficult and time consuming it is to maintain data integrity when manipulating, referencing, extracting, and/or exporting tabular data.

At step 335, the method includes labeling the common data as describing a single entity.

At step 337, the method includes storing the extracted data of step 333 as an autonomous entity under the label of step 335. The data stored at step 333 remains autonomous, as described above. This means the stored data is safe to process without any knowledge of any other data and without corrupting any of the other received data. In an embodiment, the data is stored as a JSON file or another language-independent file format. In some embodiments, the stored data may be combined or nested with additional data. Again, using the exemplary tabular data of FIG. 4F, export entity 406b might be nested within export entity 406d. Even further, export entity 406a may be nested within export entity 406b, thereby storing export entities as multi-level nested structures/files.

At step 339 of FIG. 3C, the method for standardizing and converting data into an export entity includes linking a plurality of single entities to create a master file (e.g., file 408 of FIG. 4F).

In an embodiment, each transaction described in FIG. 3C is recorded as a transaction record that is stored in an auditable persistent file. In other words, as the data is sorted, extracted, labeled, stored, and linked, as described in FIG. 3C, the data transactions are recorded in a manner that may be later reviewed or audited. For example, if a column of a tabular input data file is modified such that the name of the column changes, a transaction record may include a description of the modification, reason for the modification, and it may include other data describing the old and new column name. This aspect allows a user to troubleshoot possible errors in the classification of the column and to better understand how the data was transformed.

While performing step 311, the system may encounter a fault condition. Depending on the nature of the fault condition, the fault handler 240 may either attempt to fix the faulty data or remove it from the data file and continue processing the data. In some embodiments, fault handler 240 will require human intervention (as described in FIG. 5, below). In such embodiments, ingester 205 may generate an alert notifying an administrator of the fault condition. Furthermore, the system may continue processing the data regardless of whether human input has been received because the system can bypass or remove the mismatching demographic information until the human input is received, thereby keeping the method fault tolerant.

Returning again to FIG. 3B, at step 313, after standardizing and converting the revised data file into an export entity (e.g. export entities 306, 406a-e, or 408), the system transmits the export entity to one or more remote computers over a network. In embodiments, the remote computers may be data source(s) 105 or the remote computers may be associated with (or controlled by) a third-party health insurance provider, healthcare provider, and/or billing agency.

As explained above, when the system encounters a fault condition, the fault handler 240 may either attempt to fix the mismatching demographic information or remove the mismatching demographic information from the input data file and resume/begin processing the input data file. In some embodiments, fault handler 240 will require human intervention.

FIG. 5 illustrates an exemplary embodiment of a method for processing user input related to data that triggered a fault condition. At step 551, the system provides a notification to a user that a request for human intervention has been generated based on the detected fault condition. As used herein, a fault condition may be triggered by a corrupt file or a file containing corrupt data, an unknown column, a mislabeled column, duplicative data types in neighboring columns, multiple address blocks (e.g., address 1, zipcode 1, address 2, zipcode 2, etc.), a different number of city codes than address blocks, incongruent number of related data types (e.g., number of licenses compared to license expiration dates; number of addresses compared to number of zip codes; number of first names compared to number of surnames), a known/required column is missing or undetected (e.g., the system expects to see a column that is absent from the data), and any other condition indicating a mislabeled, unexpected, duplicative, or unknown data type.

At step 553, the system causes the notification to be displayed at a user interface. As used herein, a user interface includes a touchscreen, screen, or device that allows a user to interact with a computer. In an embodiment, the notification may be displayed on a screen as a graphical user interface (GUI). In such embodiments, the user may interact with the user interface using the touchscreen or using a keyboard, keypad, mouse, dial, or any other interface capable of interacting with a GUI. In an embodiment, the system may suggest a possible data type based on a probability that the data type was identified correctly. For example, as provided above with respect to step 303 (of FIG. 3B), ingester 205 may generate a score indicating a probability that each of the plurality of fields of demographic information was identified correctly. In embodiments where the probability score does not meet a specific threshold, it may trigger a fault condition that requires a human user to confirm the data type. In such embodiments, the system may suggest possible data types based on the probability score.

At step 555, the system receives, at the user interface, a user input in response to the human intervention notification. For example, in an embodiment when a fault condition is triggered upon detecting a corrupt file or corrupt data within a file, a user may be provided several options (e.g. several GUI buttons) to determine how the system should react. The buttons may include, for example, "perform a file scan," "provide a previous version of the data file," "upload a different version of the data file," "ignore," or any other action that a person of ordinary skill might perform to correct a corrupted file or a file that contains corrupt data.

In an additional embodiment, when a fault condition is triggered upon encountering mislabeled, unexpected, duplicative, or unknown data, the system may highlight or display the relevant data. The system may ask the user whether the mislabeled, unexpected, duplicative, or unknown data may be resolved. The user may resolve the issue by inputting a response via the user interface. For example, in the second row of FIG. 4A, the listed address includes a close-parenthesis symbol. The system and machine learning algorithm described herein would likely resolve this error without human intervention, but if this parenthesis symbol triggered a fault condition, a user would be asked to resolve the issue. Here, the user would indicate that the parenthesis symbol was a typo, would correct the typo by entering the number "zero," and would assign the data as a zip code under column Addrs. Similar situations may arise when data appears to be mislabeled or in an unexpected format. For example, in a column labeled "Name," if each row contains numerical data, a fault condition may be triggered to allow a human user to assign a correct label. In such an embodiment, the user may input/indicate, via the user interface, that the column should instead be labeled "license number." A person of ordinary skill would understand that this concept could be applied to other unexpected, duplicative, or unknown data that may appear in a row, a column, or a cell of a tabular formatted data input file. In an embodiment, the user may indicate that the data is not fixable, is incompressible, or for another reason should be excluded from further processing.

At step 557, the system assigns an active label to the data, or dataset, based on the received user input. In an embodiment, the active label replaces a passive label given at step 303 (of FIG. 3B). In additional embodiments, the active label may be the first label assigned to the data or dataset. In yet additional embodiments, the system may assign an active label to the data indicating that the data is incomprehensible and should be excluded from the dataset.

At step 559, the system stores the received user input and/or the assigned active label in a memory. In an embodiment, the received user input and/or the assigned active label may be stored in the same repository as step 309 (of FIG. 3B).

In summary, FIGS. 3A-B illustrate embodiments of a method for a fault-tolerant computer-implemented method of identifying demographic information in a data file and embodiments of a method for converting tabular personal demographic information into an entity file.

Figure 6B:
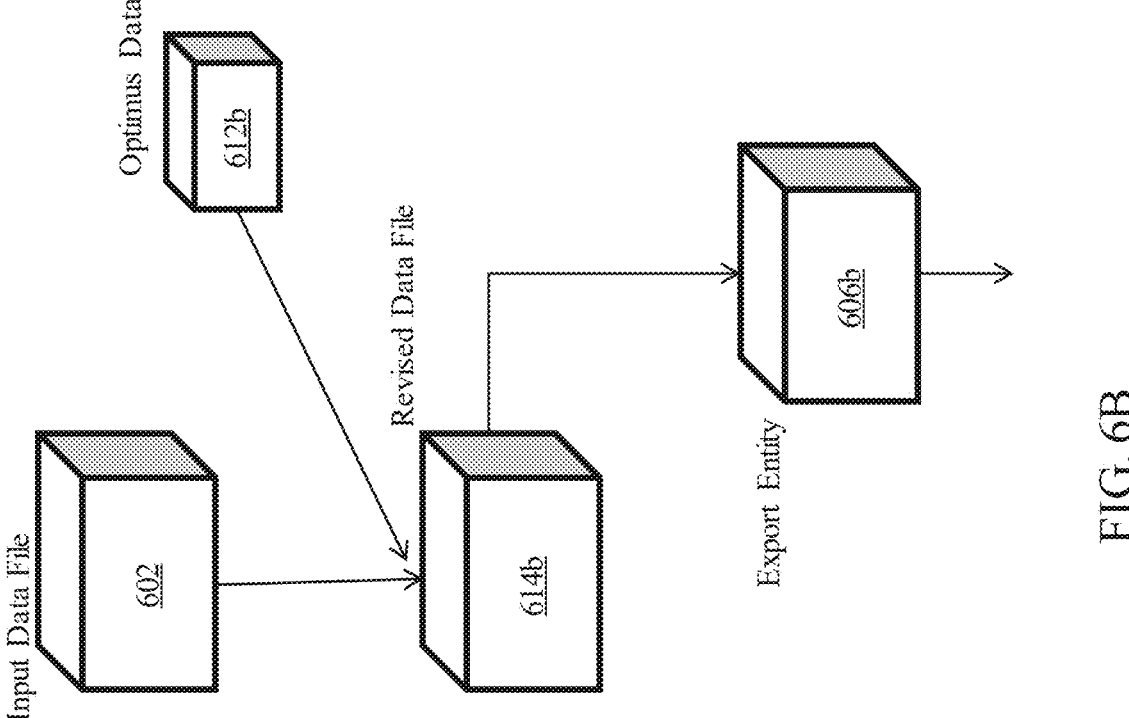
FIGS. 6A-C illustrate diagrams of methods for transforming data and converting the transformed data into export entities according to aspects of the present disclosure.
Figure 6A:
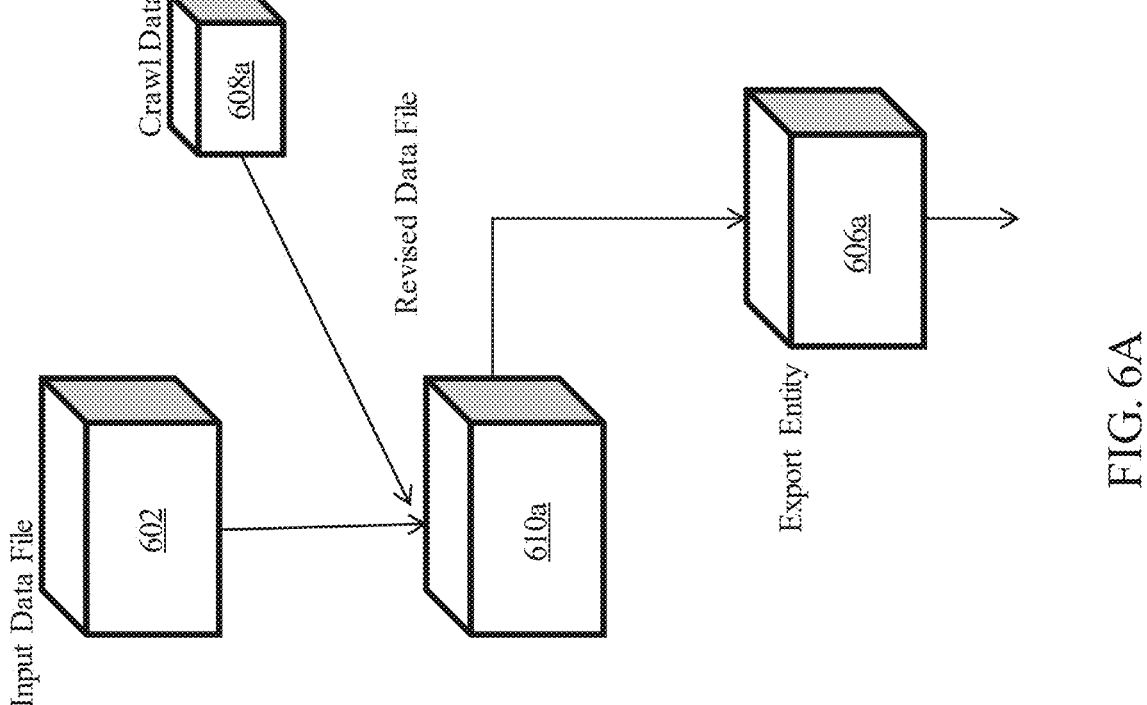
Figure 6C:
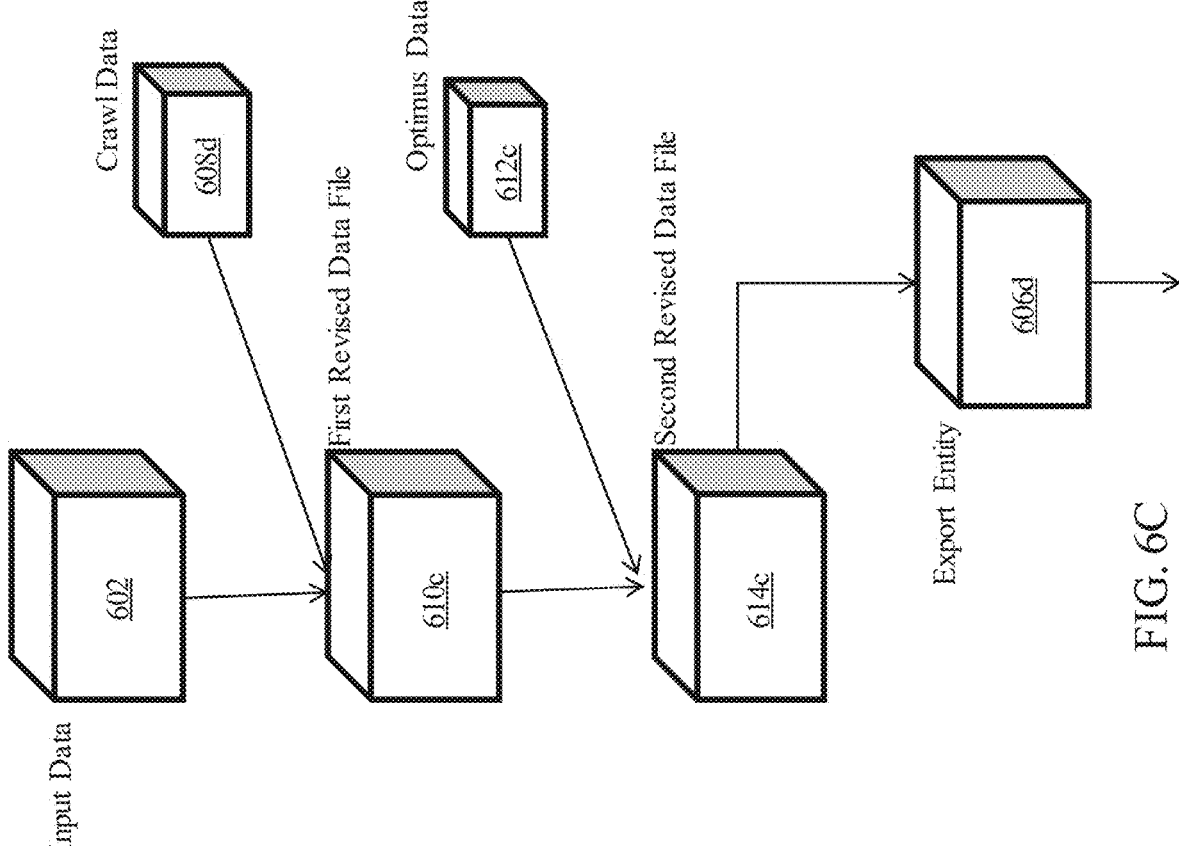

Additional embodiments and aspects are illustrated in FIGS. 6A-C. For example, FIG. 6A illustrates a method for a fault-tolerant computer-implemented method of identifying demographic information in a data file and embodiments of a method for converting tabular personal demographic information into an entity file, similar to that of FIGS. 3A-B. However, in FIG. 6A, revised data file 610*a* is not only generated by analyzing, identifying, and/or transforming the received input data file (as described in step 303 of FIG. 3B), FIG. 6A further includes comparing input data file 602 against web crawl data 608*a*.

Methods for obtaining web crawl data 608*a* will now be discussed, with reference to FIGS. 2 and 7-10. First, returning to FIG. 2, in some embodiments, one or more scouters 215 may be configured to explore all possible permutations of each data source 105 to arrive at a site of each individual listed on data source 105. To achieve this, model trainer 235 may be used to train the one or more scouters 215 using machine learning algorithms to iteratively navigate a respective data source 105 until reaching the site of each individual. For example, each scouter 215 may be trained to select a combination of one or more of a series of links, drop-down menus, radial buttons, etc., until a path to the site of each individual is determined. In some embodiments, the series of links, drop-down menus, etc. may include one or more parameters for searching for healthcare providers. The parameters may include a county, zip code, city, specialty, languages spoken, insurances accepted, and the like. It should be understood by those of ordinary skill in the arts that these are merely example parameters and that any combination of parameters may be used in accordance with aspects of the present disclosure.

In some embodiments, scouters 215 may be trained, for example, using supervised machine learning algorithms based on sample data sources to learn how to navigate the data sources to the sites of each individual. For example, using the sample data sources, scouters 215 may be trained on how to select a combination of the one or more of a series of links, the drop-down menus, the radial buttons, etc. That is, scouters 215 may be trained on set of training examples (e.g., sample data sources), such that scouters 215 may navigate the data sources 105 without human intervention. An example of supervised machine learning algorithms that may be used to train scouters 215 include, but are not limited to, support vector machines, linear regression, logistic regression, naive Bayes, linear discriminant analysis, decision trees, k-nearest neighbor algorithm, neural networks, and similarity learning. It should be understood by those of ordinary skill in the art that these are merely example supervised machine learning algorithms and that other supervised machine learning algorithms may be used in accordance with aspects of the present disclosure.

In some embodiments, one or more scouters 215 may generate a decision tree for a respective data source 105 that provides a route to the site of each individual. That is, scouters 215 may generate a decision tree for each of a plurality of data sources with the decision tree comprising one or more paths to respective sites of the data source 105.

Figure 7:
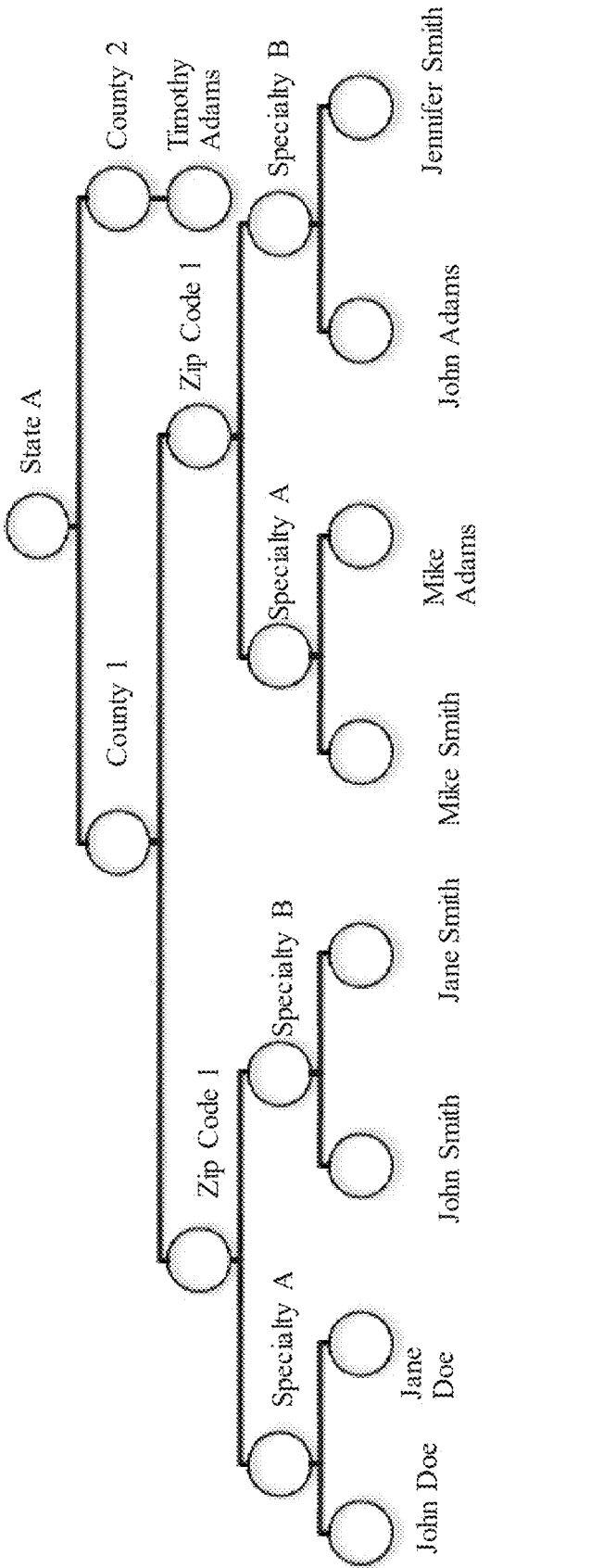
FIG. 7 illustrates an example decision tree generated by the system for accumulating data from the one or more data sources, according to aspects of the present disclosure.

As one example, FIG. 7 illustrates a decision tree for state A that includes the parameters county, zip code, and specialty. It should be understood that the parameters shown in FIG. 7 are merely example parameters, and that any combination and/or order of parameters may be used to navigate to the site of each individual.

Furthermore, in some instances, the decision tree may include multiple branches to the same site of an individual (i.e., fewer search parameters are required to reach the site of each individual), and in such instances, scouter 215 may retain the shortest path to the site of the individual while discarding all remaining paths to the site of the individual. Furthermore, scouter 215 may routinely survey the respective data source 105 to determine if any updates and/or modifications have been made (e.g., whether any healthcare providers have been added to/removed from the data source, whether the previous paths are still valid, whether any shorter paths have been established, etc.). For example, scouter 215 may survey a data source 105 for updates and/or modifications weekly, monthly, quarterly, etc. In some embodiments, controller 220 may maintain a schedule for surveying data sources 105 and instruct scouter(s) 215 to survey data source 105 accordingly.

Using the decision tree generated by one or more scouters 215, controller 220 may generate and maintain a list of tasks for each of the plurality of data sources 105. In some embodiments, each task may correspond to a respective one of the one or more paths to navigate from a base web site to a destination, leaf web site that includes the desired demographic information. Each task may also include instructions for extracting demographic information from the respective site. That is, controller 220 may split the decision tree into separate tasks having instructions for obtaining the demographic information from the site of each individual. In some embodiments, controller 220 may communicate these tasks to a corresponding data extractor 211, with the task providing the corresponding data extractor 211 with instructions on how to extract the demographic information from the respective site. For example, controller 220 may assign and transmit the task to the corresponding data extractor. As another example, controller 220 may store the tasks in a queue such that the data extractor 211 may select one of the tasks from the queue. The task communicated to the data extractor 211 may cause the data extractor 211 to navigate the corresponding data source to the respective site and extract the demographic information from the respective site. Furthermore, controller 220 may track which tasks have been communicated to data extractors 211 in order to ensure that data extractors 211 avoid performing duplicate tasks. In some embodiments, one or more data extractors 211 may be a computing device, such as a mobile phone (e.g., a smart phone, a radiotelephone, etc.), a laptop computer, a tablet computer, a handheld computer, or a similar type of device.

The instructions may include instructions for navigating through data source 105 to the respective site. For example, the instructions may indicate which link(s) to click, which drop-down option(s) to select, which radial button(s) to select, or the like, in order to navigate to the respective site.

To achieve this, the instructions may also include instructions for emulating movements of a user when navigating data source 105. That is, the instructions may indicate where to move the mouse on a given site to make the aforementioned selections. Additionally, the instructions may include instructions to move the mouse after clicking the particular link, selecting an option of the drop-down list, selecting a radial button, or the like. Further embodiments may include instructions for obviating a challenge-response test (e.g., a completely automated public Turing test to tell computers and humans apart "CAPTCHA"). For example, the instructions may direct the data extractor 211 to access a specific uniform resource locator ("URL"), rather than navigating through data source 105. In some embodiments, the instructions for navigating through data source 105 may include instructions that cause the data extractor 215 to automatically navigate to a given page, e.g., a "Contact Us" page, of data source 105 and extract the demographic information from the given site.

In some embodiments, controller 220 may communicate the tasks to the data extractors 211 based on a combination of a priority level of a data source 105 and a random selection. To achieve this, the data sources 105 may be assigned a priority level. For example, as illustrated in FIG. 8, the data sources 105 may be assigned a high priority, a moderate priority, or a low priority.

As illustrated in FIG. 8, the priority levels may be assigned to different states, different regions, different insurance providers, etc. It should be understood by those of ordinary skill in the arts that these are merely example priority levels, and that any number of priority levels are further contemplated in accordance with aspects of the present disclosure. In some embodiments, for any given priority level, controller 220 may communicate the tasks from a randomly selected data source 105 within a given priority level to corresponding data extractors 211. In some embodiments, the priority level for each data source 105 may be set by an administrator of the system 115 and may be adjusted any time.

Controller 220 may manage the number data extractors performing tasks for a corresponding data source 105. For example, in some embodiments, managing the number of data extractors may include managing a maximum number of data extractors 211 performing tasks on each of the plurality of data sources 105. That is, to avoid overloading data source 105, the controller 220 may limit the number of data extractors 211 performing tasks on a given data source 105. When the maximum number of data extractors for a given data source 105 is reached, controller 220 may communicate task(s) of another data source 105 having the same priority level to a corresponding data extractor(s) 211. Additionally, or alternatively, when the maximum number of data extractors for a given data source is reached, controller 220 may communicate task(s) of another data source 105 having a different priority level to a corresponding data extractor(s) 211. In some embodiments, the other data source 105 of the same or different priority level may be randomly selected.

In further embodiments, managing the number data extractors may include periodically adjusting the number of data extractors 211 performing tasks on a data source 105 to increase or decrease the workload on data source 105. For example, controller 220 may periodically adjust the number of data extractors 211 performing tasks on a data source 105 in order to avoid overloading data source 105 or to maximize the load on data source 105 during off-peak usage hours (e.g., overnight). In some embodiments, after reducing the number of data extractors 211 performing tasks on data source 105, controller 220 may reassign data extractors 211 to perform tasks on another data source 105 having the same priority level. Additionally, or alternatively, controller 220 may reassign the data extractors 211 to perform tasks on another data source 105 having a different priority level. In some embodiments, the other data source 105 of the same or different priority level may be randomly selected.

In some embodiments, controller 220 may also generate a user interface presented on a display 230. For example, the user interface may indicate a color code indicator of the priority level of a data source 105, the number of tasks for each data source 105, an identification number of data source 105, the number of data extractors 211 performing tasks on each data source 105, a progress indicator of the tasks for each data source 105 (e.g., a percentage of jobs completed, whether data extractors 211 have started or completed the tasks, etc.), and an overall status of the tasks (e.g., "none," "executing," "initialized," "completed," etc.). Using the user interface, an administrator may pause one or more data extractors 211 from performing tasks on data source 105 and/or change the priority level of a data source 105. In some embodiments, the user interface may be updated in predetermined intervals, e.g., every 15 minutes, every hour, etc.

In further embodiments, controller 220 may also maintain a schedule for each data source 105 indicating when data source 105 should be crawled in order to obtain the demographic information. For example, each data source 105 may be crawled based on its own respective schedule (e.g., daily, weekly, bi-weekly monthly, bi-monthly, quarterly, etc.). Using these schedules, controller 220 may determine whether to obtain the demographic information from a specific site of a given data source 105. For example, when given data source 105 is scheduled for crawling, controller 220 may communicate a message to one of data extractors 211 with a script for exploring data source 105. After a job is completed, controller 220 may receive a message from data extractor 211 indicating that the job is complete and also requesting a new job.

In some situations, data extractor 211 performing a given task may encounter a failure at data source 105 (e.g., data source 105 itself or the site of each individual is inaccessible). To resolve this, the script may include instructions for repeating the task when data extractor 211 encounters the failure. For example, the instructions may cause data extractor 211 to iteratively attempt to access the site of an individual at a set interval and for a set number of attempts (e.g., every twenty-four hours for three days). If data extractor still encounters the failure, the instructions may cause data extractor 211 to notify controller 220 indicating such, and in response, controller 220 may dispatch scouters 215 to determine another path to the site of the individual, determine if the site of each individual is no longer active, or determine if data source 105 itself is inaccessible.

In some embodiments, data extractors 211 may be trained using machine learning algorithms to accumulate unstructured demographic data from data sources 105 in a structured manner. For example, model trainer 235 may be used to train data extractors 211, for example, using supervised machine learning algorithms to learn, identify, and extract the unstructured data on any given site. For example, using the sample data sources, data extractors 211 may identify a distance between two or more parameters, e.g., a name and address of a healthcare provider on a rendered image of a given site of the data source. For example, the distance between the two or more parameters may be a vertical distance (e.g., the parameters are vertically aligned) or a horizontal distance (e.g., the parameters are horizontally aligned). As another example, the distance between the two parameters may be the distance between x-y coordinates of each parameter in a rendered image of the site. In other words, in some embodiments, the distance between two parameters may be a spatial distance. It should be understood by those of ordinary skill in the art that the name and address are merely examples of demographic information, and that data extractors 211 may be trained to identify other types and combinations of demographic information. As another example, data extractors 211 may be trained to identify a number of pairs of parameters on a given site of data source 105. That is, in some situations, multiple healthcare providers may be listed on the same site with common demographic information or unique demographic information associated with each healthcare. In further embodiments, data extractors 211 may be trained to identify a ratio between a number of healthcare providers and a number of pieces of demographic information. As a further example, data extractors 211 may be trained to identify the demographic information based on a code used to generate the site. For example, data extractors 211 may identify the distance between the demographic information in marked-up language (e.g., XML or Hypertext Markup Language (HTML) code) on any given site. For example, the code for each site may include a nested node or trees, and the distance between the demographic information and the node may be a number of steps between the nested code or tree of the different types of demographic information. Additionally, data extractors 211 may identify line number and character number of each of the parameters and determine a distance between them.

Data extractors 211 may be trained to identify whether the various pieces of demographic information are related to one another. For example, the distances, number of pairs of parameters, and/or ratio between a number of healthcare providers and a number of pieces of demographic information may be features inputted to generate a model. Model trainer 235 may use a sample set generated by humans identifying related demographic information on the same page or by analyzing a sample set of pages with known positions or labeling of related demographic information. The labeling may be, for example, within tags in the markup language.

Using this training, data extractors 211 may identify any combination of demographic information on each respective site of a data source 105. That is, data extractors 211 may be trained on a set of training examples (e.g., sample data sources), such that data extractors 211 may identify and extract the unstructured data on any given site without human intervention. Example supervised machine learning algorithms that may be used to train scouters 215 include, but are not limited to, support vector machines, linear regression, logistic regression, naive Bayes, linear discriminant analysis, decision trees, k-nearest neighbor algorithm, neural networks, and similarity learning. It should be understood by those of ordinary skill in the art that these are merely example supervised machine learning algorithms and that other supervised machine learning algorithms may be used in accordance with aspects of the present disclosure.

After identifying and extracting the unstructured demographic data, the data extractors 211 may reformat the demographic data in a structure manner. For example, as illustrated in FIG. 9, the data extractors 211 may generate a report having the data retrieved from the sites in a table format.

In the example, shown in FIG. 9, the structured format may include first name, last name, address, phone number, email address, specialty, license number, and expiration date. It should be understood by those of ordinary skill the art that this is merely an example report and that reports having different types of demographic information may be generated in accordance with aspects of the present disclosure. In some embodiments, the data extractors 211 may transmit the report to the server 200, which may then process the report. For example, ingester 205 may retrieve the demographic data from the report of the data extractors 211 and separate the demographic information based on the category of data (e.g., name, address, phone, specialty, etc.) into separate databases within the repository 225. For example, the different categories of data may be separated into logical partitions within the repository 225. Alternatively, the different categories of data may be separated into different memories within the repository 225. In other words, ingester 205 retrieves all of the demographic data accumulated for a given data source 105, identifies and categorizes the various pieces of information collected based on a category of data, and stores the categorized data within an assigned partition or database within the repository 225. In further embodiments, ingester 205 may monitor each data source 105 to determine whether data relating to any individual has changed and requires updating.

FIG. 10 illustrates a method of extracting unstructured data from a plurality of data sources, according aspects of the present disclosure. For example, a method 1000 may include generating a decision tree for each of a plurality of data sources 1005. The decision tree may comprise one or more paths to respective sites of the data source. For example, one or more scouters (e.g., scouters 215 of FIG. 2) may be configured to explore all possible permutations of each data source (e.g., data sources 105 of FIG. 1) to arrive at a site of each individual listed on the data source. This may include selecting a combination of one or more of a series of links, drop-down menus, radial buttons, etc., until a path to the site of each individual is determined.

The method 1000 may also include generating a list of tasks for each of the plurality of data sources (e.g., data sources 105 of FIG. 1) based on the decision tree 1010. Each task may correspond to a respective one of the one or more paths and may comprise instructions for extracting demographic information from the respective site. For example, a controller (e.g., controller 220 of FIG. 2) may split the decision tree into separate tasks having instructions for obtaining the demographic information from the site of each individual. The method 1000 may also include assigning a task from the list of tasks to a corresponding data extractor based on a priority level of the corresponding data source 1015. For example, the controller (e.g., controller 220 of FIG. 2) may assign these tasks to a corresponding data extractor (e.g., the data extractor 211 of FIG. 2), with the task providing the corresponding data extractor with instructions on how to extract the demographic information from the respective site.

The method 1000 may also include causing the corresponding data extractor to navigate the corresponding data source to the respective site and extract the demographic information from the respective site based on the assigned task 1020. For example, the controller (e.g., controller 220 of FIG. 2) may transmit the assigned task to the corresponding data extractor (e.g., the data extractor 211 of FIG. 2), which causes the data extractor to navigate the corresponding data source to the respective site and extract the demographic information from the respective site based on the assigned task. The method 1000 may also include receiving the extracted demographic information 1025 from the corresponding data extractor. For example, the corresponding data extractor (e.g., the data extractor 211 of FIG. 2) may transmit the extracted data to a server (e.g., the server 200 of FIG. 2).

The method 1000 may further include parsing the extracted demographic information into separate categories 1030 and storing the parsed demographic information in separate databases based on the separate categories 1035. For example, an ingester (e.g., ingester 205 of FIG. 2) may be configured to retrieve the demographic data accumulated by the data extractors (e.g., the data extractor 211 of FIG. 2) and separate the demographic information based on the category of data (e.g., name, address, phone, specialty, etc.) into separate databases within a repository (e.g., the repository 225 of FIG. 2). In some embodiments, the different categories of data may be separated into logical partitions within the repository (e.g., the repository 225 of FIG. 2). Alternatively, the different categories of data may be separated into different memories within the repository (e.g., the repository 225 of FIG. 2).

Returning to FIG. 6A, the system compares web crawl data 608*a* against input data file 602 and the data obtained by analyzing, identifying, and/or transforming the input data file (as described at step 303 of FIG. 3) to provide a more accurate revised data file 610*a*. Revised data file 610*a* is then processed according to the steps of FIGS. 3B-C and 5 to generate export entity 606*a*.

FIG. 6B illustrates a method for a fault-tolerant computer-implemented method of identifying demographic information in a data file and embodiments of a method for converting tabular personal demographic information into an entity file, similar to that of FIGS. 3A-B. However, in FIG. 6B, revised data file 614*b* is not only generated by analyzing, identifying, and/or transforming the received input data file (as described in step 303 of FIG. 3B), FIG. 6B further includes comparing input data file 602 against optimus data file 612*b*.

As explained above, after analyzing, identifying, and/or transforming the received input data file (e.g., step 303 of FIG. 3B), the system stores the revised data file in a repository (e.g., at step 309 of FIG. 3B). Furthermore, in cases where a fault condition is triggered, additional user input may be received and stored (e.g., step 559 of FIG. 5). Together, or separately, this stored data may form optimus data file 612*b* for a specific data source. As new data becomes available, or as new data is processed using the methods described herein, optimus data file 612*b* may be updated to include the most current data describing a specific data source.

Comparing optimus data 612*b* against input data file 602 and the data obtained by analyzing, identifying, and/or transforming the input data file (as described at step 303 of FIG. 3) provides a more accurate revised data file 614*b*. Revised data file 614*b* is then processed according the steps of FIGS. 3B-C and 5 to generate export entity 606*b*.

In an embodiment, export entity 606*b* may be a delta file comprising the differences between the analyzed, identified, and/or transformed input data file (as described at step 303 of FIG. 3) and optimus file 612*b*.

FIG. 6C illustrates a method for a fault-tolerant computer-implemented method of identifying demographic information in a data file and embodiments of a method for converting tabular personal demographic information into an entity file, similar to that of FIGS. 3A-B. However, FIG. 6C further includes comparing input data file 602 against web crawl data 608*d* (as described with respect to FIG. 6A) and later optimus data file 612*b* (as described with respect to FIG. 6B) to generate export entity 606*d*.

Each of the servers and modules described above can be implemented in software, firmware, or hardware on a computing device. A computing device can include but is not limited to: a personal computer, a mobile device such as a mobile phone, workstation, embedded system, game console, television, set-top box, or any other computing device. Further, a computing device can include, but is not limited to, a device having a processor and memory, including a non-transitory memory, for executing and storing instructions. The memory may tangibly embody the data and program instructions in a non-transitory manner. Software may include one or more applications and an operating system. Hardware can include, but is not limited to, a processor, a memory, and a graphical user interface display. The computing device may also have multiple processors and multiple shared or separate memory components. For example, the computing device may be a part of or the entirety of a clustered or distributed computing environment or server farm.

Figure 11:
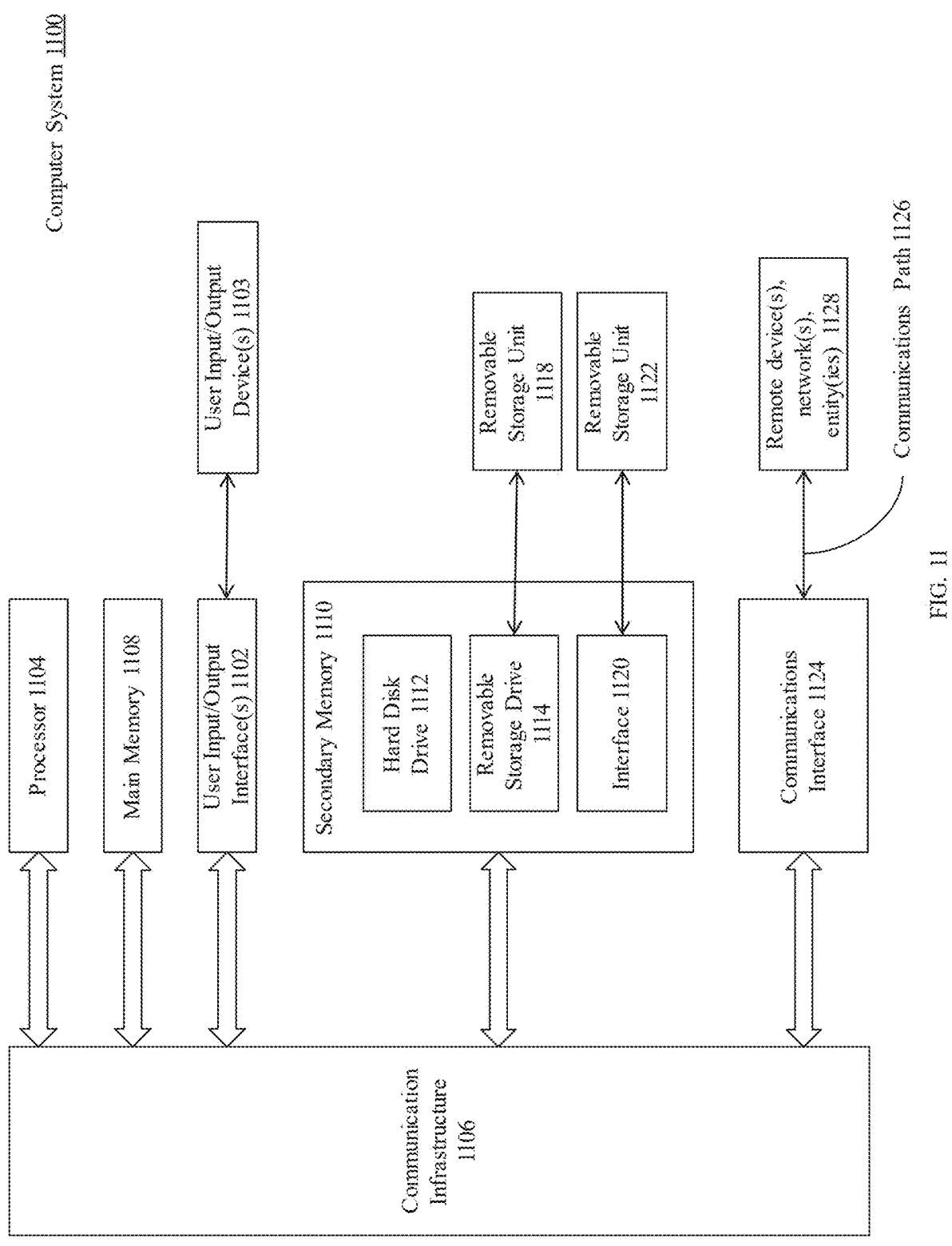
FIG. 11 is an example computer system useful for implementing various embodiments.

Various embodiments may be implemented, for example, using one or more well-known computer systems, such as computer system 1100 shown in FIG. 11. One or more computer systems 1100 may be used, for example, to implement any of the embodiments discussed herein, as well as combinations and sub-combinations thereof.

Computer system 1100 may include one or more processors (also called central processing units, or CPUs), such as a processor 1104. Processor 1104 may be connected to a communication infrastructure or bus 1106.

Computer system 1100 may also include user input/output device(s) 1103, such as monitors, keyboards, pointing devices, etc., which may communicate with communication infrastructure 1106 through user input/output interface(s) 1102.

One or more of processors 1104 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1100 may also include a main or primary memory 1108, such as random access memory (RAM). Main memory 1108 may include one or more levels of cache. Main memory 1108 may have stored therein control logic (i.e., computer software) and/or data.

Computer system 1100 may also include one or more secondary storage devices or memory 1110. Secondary memory 1110 may include, for example, a hard disk drive 1112 and/or a removable storage device or drive 1114. Removable storage drive 1114 may be a floppy disk drive, a magnetic tape drive, a compact disk drive, an optical storage device, tape backup device, and/or any other storage device/drive.

Removable storage drive 1114 may interact with a removable storage unit 1118. Removable storage unit 1118 may include a computer usable or readable storage device having stored thereon computer software (control logic) and/or data. Removable storage unit 1118 may be a floppy disk, magnetic tape, compact disk, DVD, optical storage disk, and/any other computer data storage device. Removable storage drive 1114 may read from and/or write to removable storage unit 1118.

Secondary memory 1110 may include other means, devices, components, instrumentalities or other approaches for allowing computer programs and/or other instructions and/or data to be accessed by computer system 1100. Such means, devices, components, instrumentalities or other approaches may include, for example, a removable storage unit 1122 and an interface 1120. Examples of the removable storage unit 1122 and the interface 1120 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1100 may further include a communication or network interface 1124. Communication interface 1124 may enable computer system 1100 to communicate and interact with any combination of external devices, external networks, external entities, etc. (individually and collectively referenced by reference number 1128). For example, communication interface 1124 may allow computer system 1100 to communicate with external or remote devices 1128 over communications path 1126, which may be wired and/or wireless (or a combination thereof), and which may include any combination of LANs, WANs, the Internet, etc. Control logic and/or data may be transmitted to and from computer system 1100 via communication path 1126.

Computer system 1100 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 1100 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (Saas), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 1100 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 1100, main memory 1108, secondary memory 1110, and removable storage units 1118 and 1122, as well as tangible articles of manufacture embodying any combination of the foregoing. Such control logic, when executed by one or more data processing devices (such as computer system 1100), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than those shown in FIG. 11. In particular, embodiments can operate with software, hardware, and/or operating system embodiments other than those described herein.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method, comprising:
   converting, by one or more computing devices, data in a data file into an export entity, wherein the converting comprises:
   sorting the data based on identifying a lowest number of unique entities associated with a type,
   extracting common data associated with the lowest number of unique entities,
   labeling the common data as describing a single entity,
   in response to the labeling, storing the extracted common data as an autonomous entity under a label of the labeled common data, and
   linking a plurality of single entities to generate the export entity; and
   combining, by the one or more computing devices, one or more export entities converted from the data into a combined file.

2. The computer-implemented method of claim 1, wherein the data is from a healthcare provider and the data file containing a plurality of fields of demographic information is a medical roster.

3. The computer-implemented method of claim 1, further comprising detecting, by the one or more computing devices, the type for one of a plurality of fields of demographic information.

4. The computer-implemented method of claim 1, further comprising extracting, by the one or more computing devices, the common data into a language-independent format.

5. The computer-implemented method of claim 1, wherein linking the plurality of single entities is performed via a pointer, a logical connection between entities, or data describing a first entity that is embedded within data describing a second entity.

6. The computer-implemented method of claim 1, further comprising storing, by the one or more computing devices, a transaction record of each of the converting, sorting, extracting, labeling, and linking steps in an auditable persistent file.

7. The computer-implemented method of claim 1, further comprising comparing, by the one or more computing devices, the combined file with an existing second combined file to determine a difference between the combined file and the existing second combined file.

8. A system, comprising:
   a memory; and
   at least one processor coupled to the memory and configured to perform operations comprising:
   converting data in a data file into an export entity, wherein the converting comprises:
   sorting the data based on identifying a lowest number of unique entities associated with a type,
   extracting common data associated with the lowest number of unique entities,
   labeling the common data as describing a single entity,
   in response to the labeling, storing the extracted common data as an autonomous entity under a label of the labeled common data, and
   linking a plurality of single entities to generate the export entity; and
   combining one or more export entities converted from the data into a combined file.

9. The system of claim 8, wherein the data is from a healthcare provider and the data file containing a plurality of fields of demographic information is a medical roster.

10. The system of claim 8, wherein the operations further comprise detecting the type for one of a plurality of fields of demographic information.

11. The system of claim 8, wherein the operations further comprise extracting the common data into a language-independent format.

12. The system of claim 8, wherein linking the plurality of single entities is performed via a pointer, a logical connection between entities, or data describing a first entity that is embedded within data describing a second entity.

13. The system of claim 8, wherein the operations further comprise storing a transaction record of each of the converting, sorting, extracting, labeling, and linking steps in an auditable persistent file.

14. The system of claim 8, wherein the operations further comprise comparing the combined file with an existing second combined file to determine a difference between the combined file and the existing second combined file.

15. A non-transitory program storage device having instructions stored thereon that, when executed by at least one computing device, causes the at least one computing device to perform operations comprising:
   converting data in a data file into an export entity, wherein the converting comprises:
   sorting the data based on identifying a lowest number of unique entities associated with a type, extracting common data associated with the lowest number of unique entities, labeling the common data as describing a single entity, in response to the labeling, storing the extracted common data as an autonomous entity under a label of the labeled common data, and linking a plurality of single entities to generate the export entity; and combining one or more export entities converted from the data into a combined file.

16. The non-transitory program storage device of claim 15, wherein the data is from a healthcare provider and the data file containing a plurality of fields of demographic information is a medical roster.

17. The non-transitory program storage device of claim 15, wherein the operations further comprise extracting the common data into a language-independent format.

18. The non-transitory program storage device of claim 15, wherein linking the plurality of single entities is performed via a pointer, a logical connection between entities, or data describing a first entity that is embedded within data describing a second entity.

19. The non-transitory program storage device of claim 15, wherein operations further comprise storing a transaction record of each of the converting, sorting, extracting, labeling, and linking steps in an auditable persistent file.

20. The non-transitory program storage device of claim 15, wherein operations further comprise comparing the combined file with an existing second combined file to determine a difference between the combined file and the existing second combined file.

* * * * *